(12) United States Patent
Forman et al.

(10) Patent No.: US 12,023,421 B2
(45) Date of Patent: *Jul. 2, 2024

(54) MEDICAL DEVICES FOR CONTINUOUS DELIVERY OF THERAPEUTIC AGENTS

(71) Applicant: Adenopaint LLC, Atlanta, GA (US)

(72) Inventors: Mervyn B. Forman, Atlanta, GA (US); Erik Brewer, Conshohocken, PA (US); Anthony M. Lowman, Clarksboro, NJ (US); Zaichuan Mi, Sewickley, PA (US); Edwin K. Jackson, Pittsburgh, PA (US)

(73) Assignee: Adenopaint, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/734,889

(22) Filed: May 2, 2022

(65) Prior Publication Data

US 2022/0288284 A1 Sep. 15, 2022

Related U.S. Application Data

(63) Continuation of application No. 17/003,361, filed on Aug. 26, 2020, now Pat. No. 11,331,418.

(60) Provisional application No. 62/891,829, filed on Aug. 26, 2019.

(51) Int. Cl.
| | |
|---|---|
| *A61L 31/10* | (2006.01) |
| *A61L 31/14* | (2006.01) |
| *A61L 31/16* | (2006.01) |
| *C08L 29/04* | (2006.01) |
| *C08L 39/06* | (2006.01) |
| *C09D 129/04* | (2006.01) |
| *C09D 131/04* | (2006.01) |
| *A61K 31/7076* | (2006.01) |
| *A61K 45/06* | (2006.01) |

(52) U.S. Cl.
CPC ............. *A61L 31/10* (2013.01); *A61L 31/145* (2013.01); *A61L 31/16* (2013.01); *C08L 29/04* (2013.01); *C08L 39/06* (2013.01); *C09D 131/04* (2013.01); *A61K 31/7076* (2013.01); *A61K 45/06* (2013.01); *A61L 2300/232* (2013.01)

(58) Field of Classification Search
CPC ........ A61L 31/10; A61L 31/145; A61L 31/16; A61L 2300/232; A61L 2300/42; A61L 2300/802; C08L 29/04; C08L 39/06; C08L 39/00; C09D 131/04; C09D 129/04; A61K 31/7076; A61K 45/06; C08K 5/3465
See application file for complete search history.

(56) References Cited

U.S. PATENT DOCUMENTS

| | | | | |
|---|---|---|---|---|
| 6,042,876 | A * | 3/2000 | Deem | A61M 25/09 427/2.3 |
| 11,331,418 | B2 * | 5/2022 | Forman | A61L 31/16 |
| 2009/0138077 | A1 * | 5/2009 | Weber | C23C 18/127 428/210 |
| 2009/0227946 | A1 * | 9/2009 | Kangas | A61L 29/145 522/111 |
| 2011/0150966 | A1 * | 6/2011 | Chen | C09D 167/04 514/182 |

OTHER PUBLICATIONS

Morariu, Simona, et al. "Tailoring the properties of poly (vinyl alcohol)/poly (vinylpyrrolidone) hydrogels for biomedical applications." European Polymer Journal 84 (2016): 313-325. (Year: 2016).*
Forman, Mervyn B., et al. "Development of a novel adenosine-eluting guidewire (Adenowire) for coronary vasodilation during percutaneous coronary intervention." EuroIntervention 9.11 (2014): 1323-1332. (Year: 2014).*
Arldes, B."Gelest-Hydrophobicity, hidrophilicityandsilanesurfacemodification." obtainedonlineat:httos://s3.amazonaws.com/gelest/product-brochures/Hydrophobicity-Hydrophilicity_and_Silane_Surface_Modification.pdf. (Year: 2011).*
Chaudhary,V.B.,andJ.K.Patel."Cyclodextrininclusioncomplextoenhancesolubilityofpoorlywatersolubledrugs:areview." InternationalJournalofPharmaceuticalSciencesandResearch4.1(2013):68. (Year: 2013).*
Pellinger-Tieg,Catherine.DevelopmentandinvestigationofPropranololHClpelletscoatedwithpoly(vinylacetate)basedpolymerfilmsforsustainedreleaseapplications.Diss.Universitats-undLandesbibliothekSachsen-Anhalt,2012. (Year: 2012).*
Stella VJ, Rajewski RA. Sulfobutylether-β-cyclodextrin. Int J Pharm. Jun. 15, 2020;583:119396. doi: 10.1016/j.ijpharm.2020.119396. Epub May 4, 2020. (Year: 2020).*

* cited by examiner

*Primary Examiner* — Abigail Vanhorn
(74) *Attorney, Agent, or Firm* — Ballard Spahr LLP

(57) ABSTRACT

The present invention relates to compositions and methods to provide continuous and controlled release of therapeutic agent(s) during a procedure such as an interventional vascular procedure, e.g., to reduce acute and chronic complications and improve outcomes.

19 Claims, 42 Drawing Sheets

| Coil Pitch mm (Coil spacing in) | Appearance |
|---|---|
| 0.014 (0.0006") | |
| 0.030 (0.0012") | |
| 0.043 (0.0017") | |
| 0.061 (0.0024") | |
| 0.081 (0.0032") | |
| 0.095 (0.0037") | |
| 0.109 (0.0043") | |
| 0.123 (0.0048") | |

FIG. 2

*Reaction 1:* Plasma treatment of stainless steel wires to create reactive hydroxyl groups
*Reaction 2:* Hydrolyze the PEG-Silane to form silanols
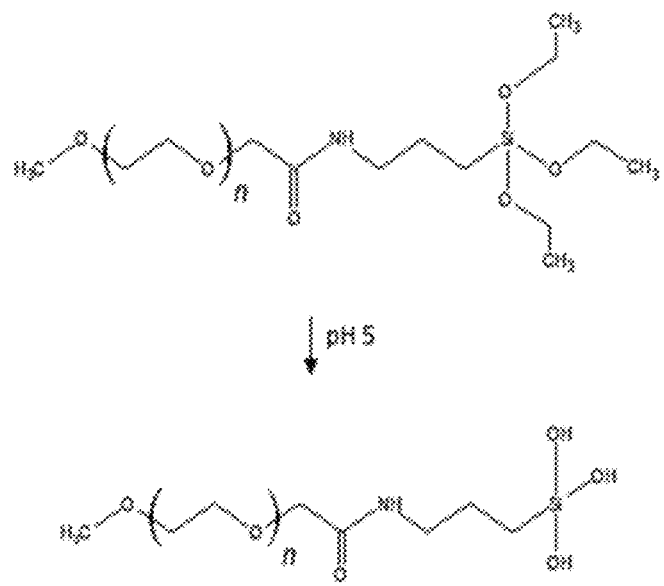
FIG. 9

*Reaction 3:* Silanols condensate to both surface hydroxyl groups and adjacent silanols to form a polymerized layer on the surface of the stainless steel wires subjected to plasma treatment to yield hydroxyl groups on the steel.

Reaction 1: Plasma treatment of stainless steel wire creates hydroxyl groups attached to the metal.

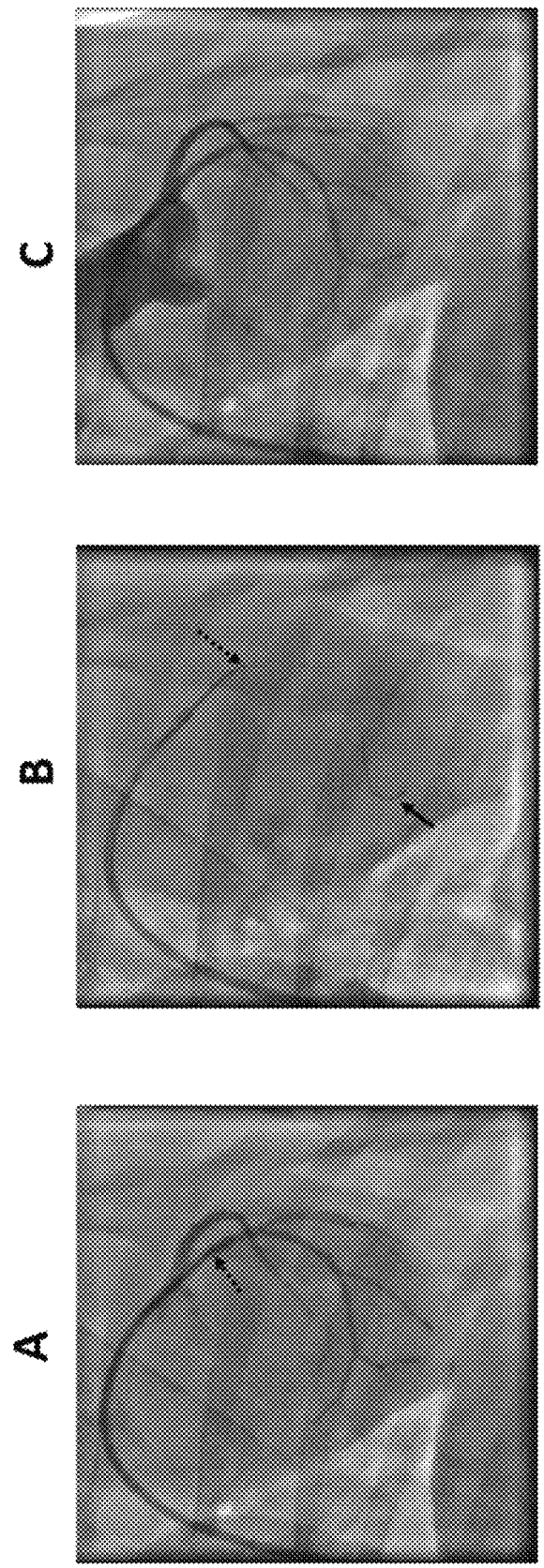
FIGs. 18A-C

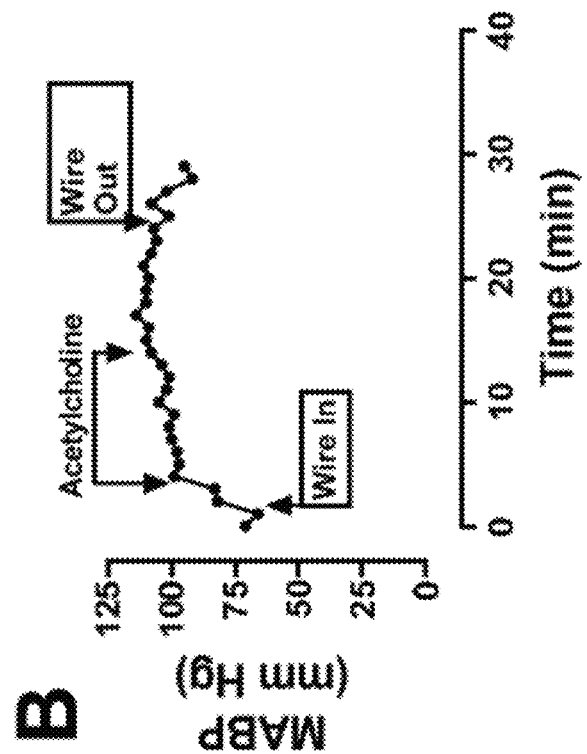
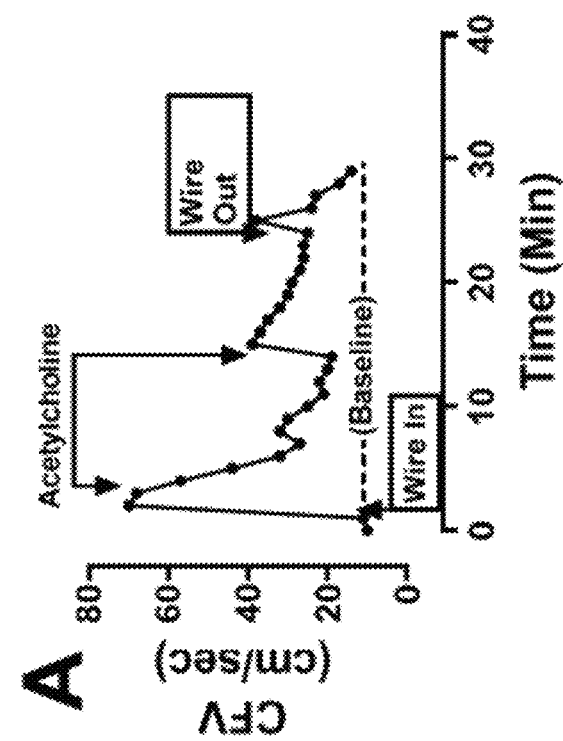
FIG. 20A
FIG. 20B

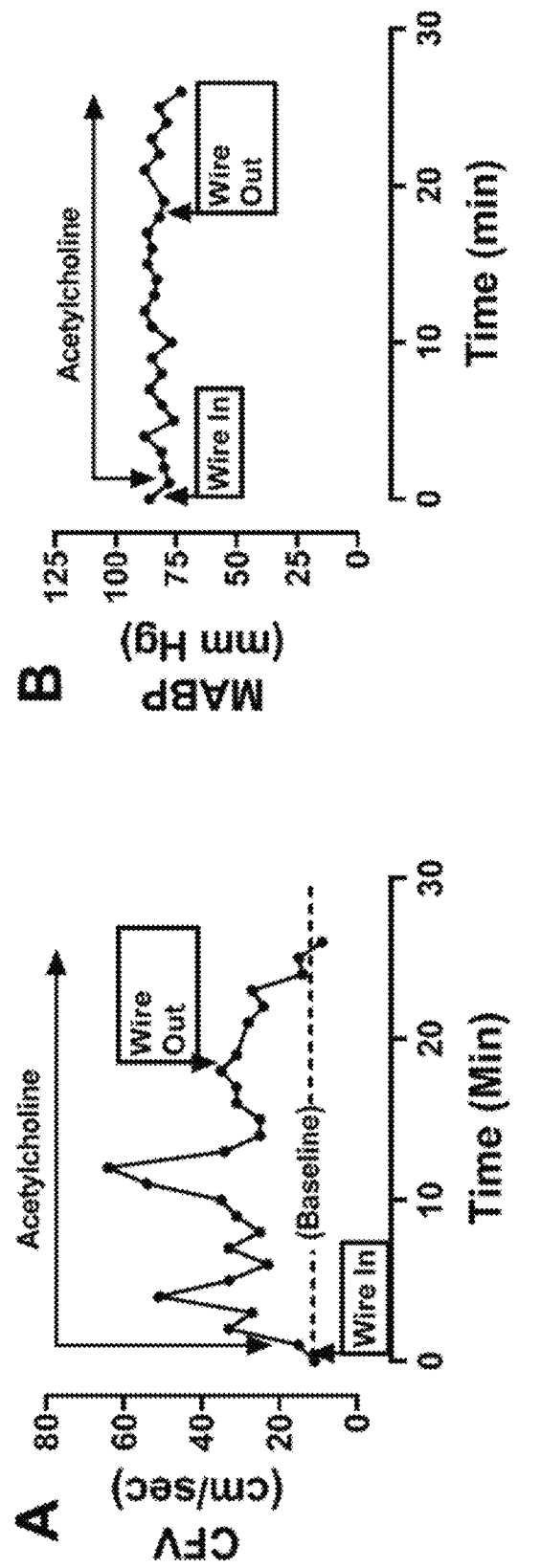

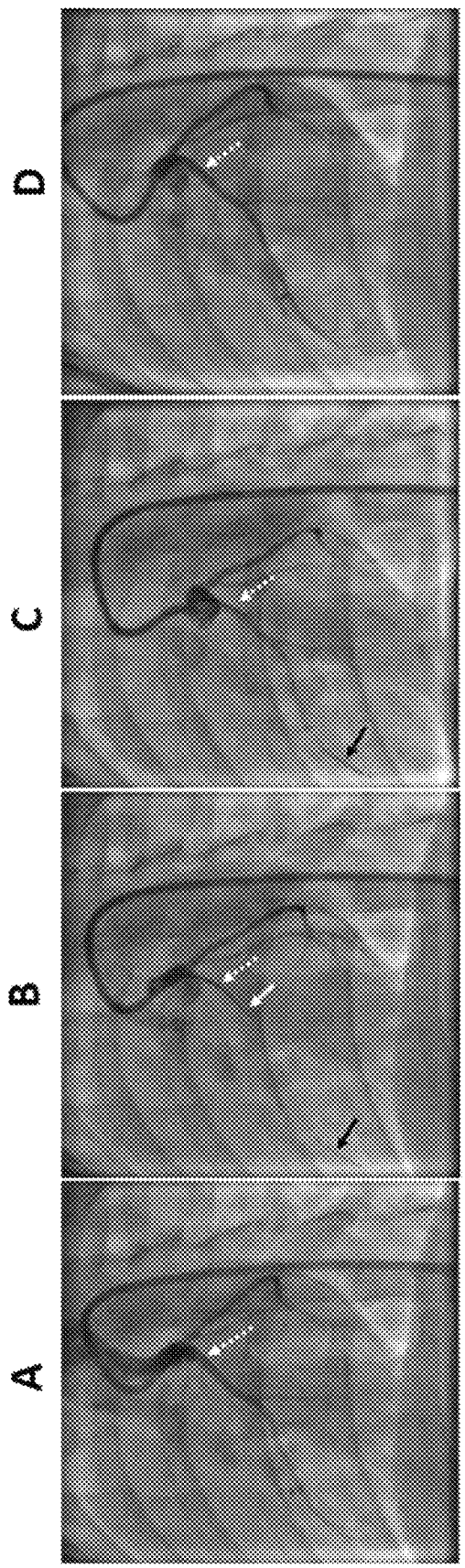
FIGs. 22A-D

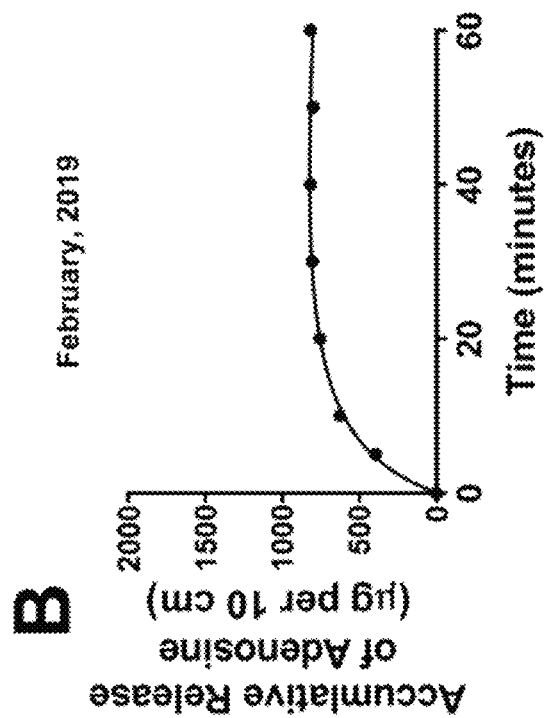
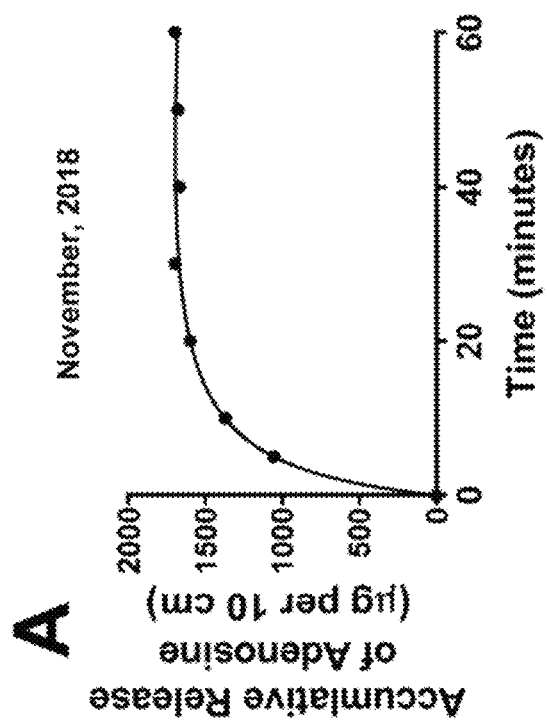
FIG. 24A
FIG. 24B

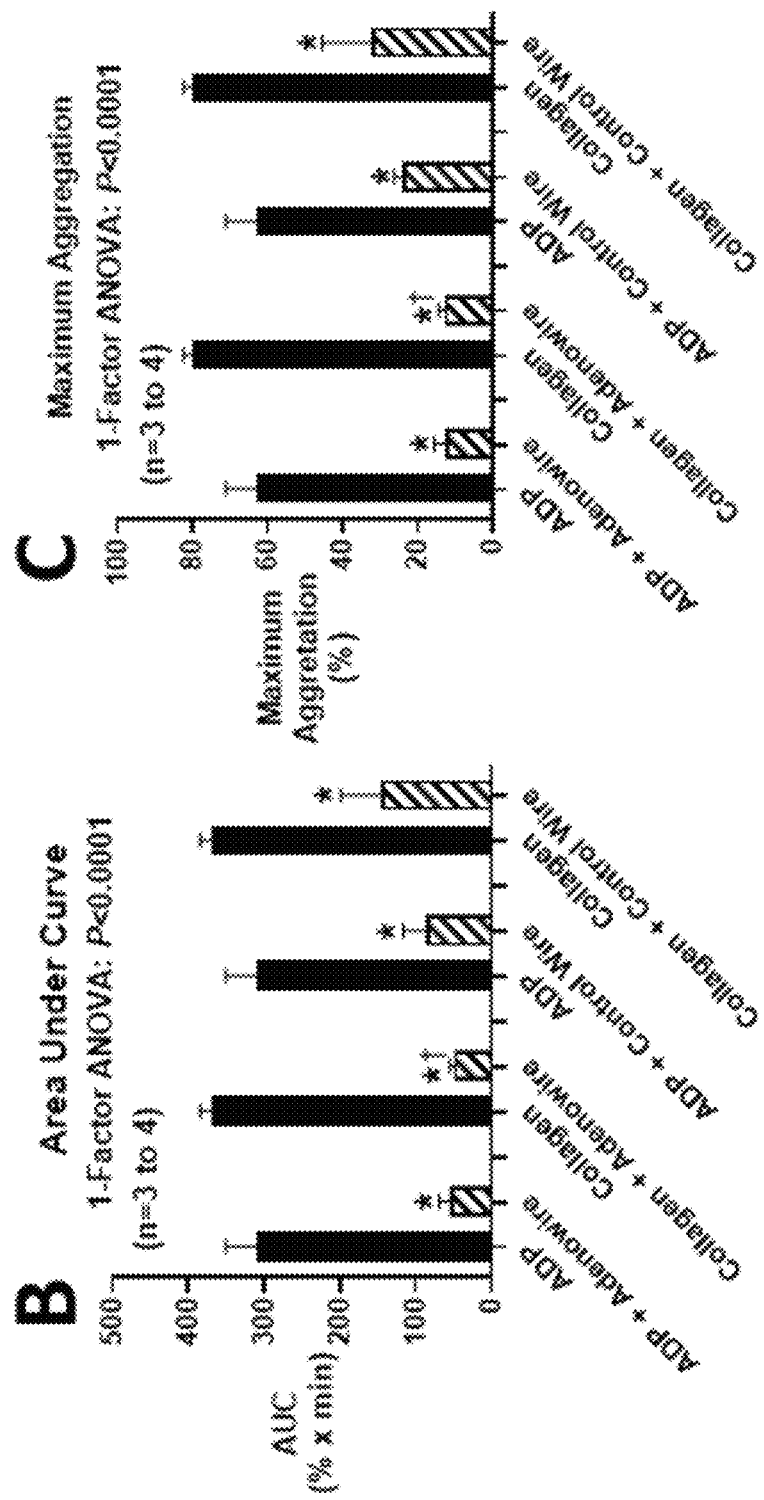
FIGs. 25B-C

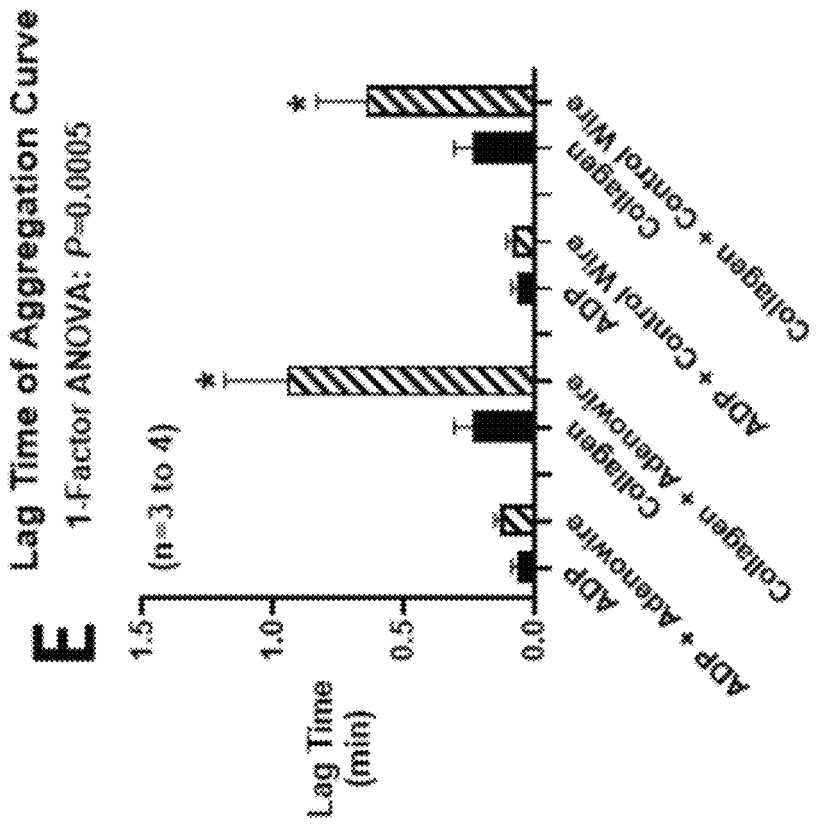
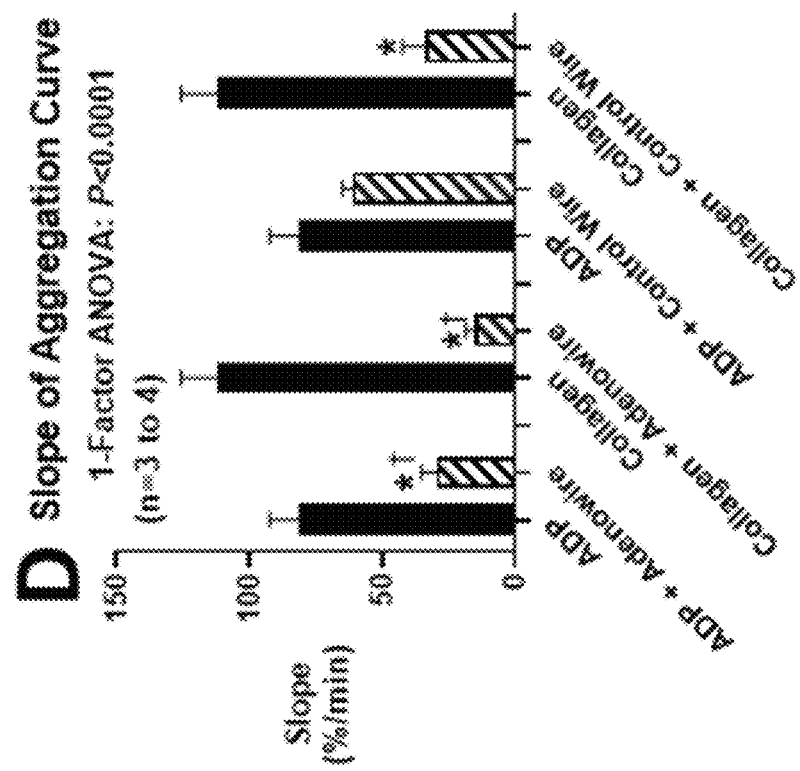
FIGs. 25D-E

MEDICAL DEVICES FOR CONTINUOUS DELIVERY OF THERAPEUTIC AGENTS

CROSS-REFERENCE TO RELATED APPLICATIONS

This application is a continuation of U.S. application Ser. No. 17/003,361, filed Aug. 26, 2020, which claims the benefit of U.S. Provisional Application No. 62/891,829, filed Aug. 26, 2019, the entirety of which are incorporated by reference.

FIELD OF THE INVENTION

The present invention relates to an insertable medical device such as a guidewire containing one or more hydrogel layers which allows for continuous release of a therapeutic agent into a subject, e.g., during a vascular procedure.

BACKGROUND

Atherosclerotic vascular disease remains a major cause of morbidity and mortality in spite of numerous advances in pharmacological modalities to modify associated risk factors. Coronary atherosclerotic vascular disease remains a leading cause of death in the developed world with over 900,000 myocardial infarctions in the US annually resulting in a mortality of 7-18% (see e.g., Go, A. S., et al., Circulation 127: e6 (2013)). Cerebrovascular disease is the third leading cause of death with stenosis of the internal carotid artery accounting for 20% of strokes and TIA's. Following the development of percutaneous balloon angioplasty (PTA) by Gruntzig in the 1970's, the procedure evolved rapidly secondary to technical advancements and the development of drug eluting stents (DES) which significantly reduced the chronic complication of restenosis. Percutaneous coronary intervention (PCI) has now surpassed CABG to treat CAD with 954,000 procedures performed in 2010 in the US alone (see e.g., Go, A. S., et al., Circulation 127: e6 (2013). Data form the European Registry (Euro PCR) showed that over 1.1 million PCI procedures were performed in 2009-10. Drivers for the increase in PCI procedures over the past decade include improvement in stent technology, aging of the baby boomer population and preference for less invasive procedures. Obesity and diabetes also contribute to the increased reliance on PCI's.

While PCI invariably restores epicardial vessel patency, the deployment of various interventional equipment into the coronary vasculature may result in acute or chronic vascular obstruction (see e.g., Forman, M. B., et al., Cardiovasc Drug Reviews 24: 116 (2006); Forman, M. B. and Jackson, E. K., Clin. Cardiol. 30:583 (2007); Nicolli, G., et al., Euro. Heart J. 31:2449 (2010)). This is more prevalent in patients with acute coronary syndromes (ACS) namely non-ST segment elevation elevation myocardial infarction (NSTEMI) or acute ST segment elevation myocardial infarction (STEMI) which occurs in the setting of an ulcerative plaque associated with a variable thrombus burden. Macro- and micro-emboli may result in impairment of tissue perfusion through microvascular obstruction (MVO) which manifests angio-graphically as the "no-reflow phenomenon" (NRF) (see, e.g., Jaffe, R., et al., J. Am. Coll. Cardiol. Intv. 3: 695 (2010); Forman, M. B., et al., Cardiovasc. Drug reviews 24:116 (2006)). The incidence of MVO varies depending on the clinical scenario and the methodology used for diagnosis. MVO manifests in 4-8% of elective procedures and disturbingly in more than 50% of STEMI's, where MVO associates with large infarct size, abnormal ventricular remodeling, arrhythmias and congestive heart failure. MVO is also an important predictor of 5-year mortality independent of infarct size (see e.g., Ndrepepa, G., et al., J Am Coll Cardiol 55: 2383 (2010)). The mechanisms responsible for MVO are complex and multifactorial and include embolization of atheromatous and thrombotic debris, release of numerous potent vasoconstrictor substances, and activation of the immune system resulting in leukocyte plugging and endothelial disruption of microvessels (see, e.g., Forman, M. B., and Jackson, E. K., Clin Cardiol 30:583 (2007), Forman, M. B., et al., Cardiovasc Drug Reviews 24:116 (2006)). The failure of a significant decrease in door-to-balloon time to reduce hospital mortality in STEMI supports the need for new avenues to improve outcomes (see, e.g., Menees, D. S., et al., New Engl. J. Med. 369:901 (2013). Recent large MRI studies emphasize the role of MVO as an independent risk factor for major cardiovascular events with greater predictive power than ejection fraction and infarct size (see, e.g., Eitl, I., et al., J. Am. Coll. Cardiol. 64: 1217 (2013), Van Kranenbury M., et al., J. Am. Coll. Cardiol. Img. 7:930 (2014)).

The realization that prevention and prompt reversal of MVO is paramount to improve outcomes in high risk PCI is motivating the evaluation of numerous devices and pharmacologic approaches to ameliorate MVO. However, studies indicate that various mechanical thrombectomy and embolic protective devices fail to improve indices of tissue perfusion, infarct size, or mortality during PCI of native coronary vessels (see, e.g., Morgeon, F. P. et al., Circ. Cardiovasc Interv. 3:6 (2010), Bates, E. R. J. Am Coll. Card Intv. 1: 265 (2008), Gick, M., et al., Circulation 12:1462 (2005), Haeck, J D. E., et al., J. Am. Coll. Cardiol. Intv. 2: 934 (2009)). Simple aspiration devices initially showed promise with the large TAPAS study reporting significant improvements in indices of microcirculatory perfusion and reduced mortality at one year (see, e.g., Svilaas, T. et al., N. Engl. J. Med. 358:557 (2008), Vlaar P. J., et al., Lancet 371:1915 (2008)). However, the TAPAS study suggests that 45% of patients still manifest no-reflow and the INFUSE trial indicates that aspiration devices do not reduce infarct size at 30 days. These observations are supported by the recent large TASTE (Thrombus Aspiration in Myocardial infarction) trial involving 7,244 patients where aspiration failed to reduce mortality or major adverse cardiac events (MACE) at 1 year (see, e.g., Lagergvist, B., et al., N. Engl. J. Med. 371: 1111 (2014). Without wishing to be bound by theory, these findings clearly demonstrate that current devices are suboptimal in reversing MVO in native vessels. While various types of embolic protection devices may significantly reduce major adverse cardiac events with PCI of degenerative saphenous vein grafts (SVG), peri-procedural infarction still occurs in approximately 8% of patients (see, e.g., Baim, D. S., et al., Circulation 105: 1285) 2002), Mauri, L., et al., J. Am, Coll. Cardiol. 50:1142 (2007), Moris, C., et al., Euro. Intervention 5: D45 (2009)). Furthermore, anatomic considerations prevent use of these devices in ~20% of saphenous vein graft PCI. Without wishing to be bound by theory, these findings demonstrate that the current devices are suboptimal in reversing or preventing embolic events. This may be related to the fact that currently available devices are not protective throughout the whole procedure and do not affect humoral factors and cytotoxic compounds responsible for MVO.

Given the importance of inadequate tissue perfusion with PCI, there is increasing awareness of the need for new pharmacological approaches to prevent and reverse MVO associated with PCI. Continuous infusions of drugs that address the various mechanisms of MVO such as vasodilators, thrombolytics, anti-inflammatory, and anti-platelet agents would offer a novel approach.

Platelet activation plays a critical role in the pathogenesis of arterial thrombotic diseases such as coronary artery disease in the setting of ACS, NSTEMI and STEMI. Cardiac catheterization and PCI amplify platelet activation and trigger the coagulation pathway secondary to the foreign surface of guidewires, catheters and contrast material. Administration of thrombolytic agents such as streptokinase and tissue-type plasminogen activator (tPA) result in further platelet activation (see, e.g., Fitzgerald, D. J., et al., Circulation 77:142 (1988). In addition to initiating further thrombus formation platelets play a key role in MVO through the release of various potent vasoconstrictor substances such as serotonin, thromboxane A2 and platelet activating factor (PAF) (see, e.g., Forman, M. B., and Jackson, E. K., Clin. Cardiol 30: 583 (2007). Platelet activation is mediated via two receptors for ADP; P2Y1 which initiates and P2Y12 which continues the process (see, e.g., Wolska, N., and Rozalski, M., Int. J. Mol. Sci. 20: 1 (2019). P2Y12 is present in the platelet plasma membrane and is the target for clinically approved inhibitors with prasugrel (thienopyridine-class) and ticagrelor (cyclo-pentyl-triando-pyrimidine) preferred because of superior effects. Efficient anti-platelet therapy is often hindered by variable sensitivity to the drugs and the necessity for high doses which lead to moderate to severe bleeding events. A novel approach would entail simultaneous delivery of lower doses of two drugs with different activation pathways directly into the coronary circulation. An example of such an approach currently used is oral administration of aspirin (inhibitor of thromboxane A2 formation) and clopidogrel (inhibitor of P2Y12). Adenosine is a purine metabolite that functions both as an important energy source in the cell but also as a signaling molecule regulating tissue function. Four adenosine receptors (A1, A2A, A2B, A3) are found in the membranes of many types of human cells and play various physiological functions (see, e.g., Forman, M. B., et al., Cardiovasc Drug reviews 24: 116 (2006). A2A receptors are highly expressed on platelet cell membranes and inhibit activation and aggregation by increasing cyclic AMP in the cell. A2A activation also reduces P-selectin expression on the platelet cell surface which occurs in the setting of thromboxane A2 and ADP stimulation. Since A2A receptors are regarded as high affinity receptors, nanomolar concentrations of agonists result in A2A receptor activation. Recently it has been shown that co-administration of 2-chloroadenosine or A2A agonists markedly enhance platelet inhibition by P2Y12 antagonists in vitro (see e.g., Boncler. M., et al., Vasc Pharm 113: 47 (2019). These results support the concept of dual platelet therapy and indicate the importance of platelet adenosine receptors as a therapeutic target.

PCI with DES may also compromise blood flow in the subacute and chronic phases after an uneventful procedure (Camenzind, E., et al., Circulation 115:1440 (2007). Subacute and chronic thrombosis may occur secondary to suboptimal stent expansion, vasospasm at site, and inadequate anti-platelet therapy. Pathological studies demonstrate chronic inflammatory cell infiltration and delayed endothelialization (Joyner, M., et al., J. Am. Coll. Cardiol., 48:193 (2006). Local delivery of drugs at PCI that accelerate endothelial healing and reduce inflammatory cell infiltration may reduce thrombosis and shorten the duration of anti-platelet therapy post stent implantation. While current DES have significantly reduced restenosis secondary to intimal proliferation to less than 10%, patients with diabetes, small vessels, and acute coronary syndromes may benefit from additional local delivery of an anti-proliferative agent.

Guidewires are the first mandatory device placed in the vessel prior to any interventional procedure and serve as a "rail-road" support system. Thus, the guidewire is defined as the first device that actually crosses the target lesion. Guidewires consist of a central mandrel with tightly wrapped coils over the distal 30 cm of the wires. Most commonly used metals for manufacture are stainless steel, nitinol, and aluminum with the tip being tungsten-platinum for radio-opacity. The coils are coated with inert hydrophilic compounds such as polyvinyl pyrrolidone (PVP), polyacrylamides, and hyaluronic acid. These rapidly absorb liquids, thereby improving lubricity of the device and enhancing the trackability through tortuous and diseased blood vessels.

Disclosure of a platform guidewire product to rapidly deliver drugs of any class without dissolution or disruption of the guidewire coating is novel and has not been taught. Hence, there is a need to modify guidewire design to allow incorporation of a suitable amount of a hydrophilic coating that is able to release medications into the vasculature immediately and continuously throughout the interventional procedure. This disclosure fulfills this unmet need by combining unique structural features of guidewire design with novel coating approaches.

Polyvinyl alcohol (PVA) is a polymer of great interest due to its many desirable properties for use in various pharmaceutical and biomedical applications (see, e.g., Hasan, C. M., and Peppas, N. A., Adv. In Polymer Science, 153: 37 (2000), Muppalaneni S., and Omidian, H., J. Developing Drugs 2: 112 (2013)). Some of these advantages include non-toxicity, non-carcinogenic and bio-adhesive characteristics, as well as associated ease of processing. PVA gels exhibit a high degree of swelling in water and biological fluids producing a rubbery and elastic quality. PVA must be crosslinked in order to be useful in a variety of applications. The crystalline nature of PVA allows physiologically cross-linking the hydrogel by repeated cycles of freezing and thawing thereby avoiding the use of potentially toxic chemical crosslinkers. The degree of crystallite formation and subsequent porous size is altered by the number of freeze/thaw cycles and concentration and molecular weight of PVA. This affects the physical properties such as mechanical strength, swelling, and drug elution properties. Crosslinked PVA hydrogels are not stable within physiological environments or after prolonged storage since they are prone to undergo dissolution. The addition of PVP or polyethylene glycol (PEG) to PVA stabilizes the hydrogel network through hydrogen bonding between the carbonyl groups of PVP or PEG and the hydroxyl groups of PVA. Due to their properties and safety, PVA hydrogels have been used in a variety of biomedical pharmacological applications. These include tissue replacement material for orthopedic applications such as cartilage for knees and intervertebral discs (see, e.g., Thomas J., et al., J. Biomed. Mater. Res. 67A 1329 (2003), Katta. J. K., et al., J. Biomed. Mater. Res. 83A 471 (2007)). Other applications include contact lens material, artificial heart linings, and skin and pancreas membranes. PVA is also used in drug delivery systems in oral, transdermal, buccal, intramuscular, and rectal routes (Langer. R., Science 249:1527 (1990), Muppalaneni, S. and Omidian. H., J. Develop Drugs 2: 112 (2013), Mallapragada, S. K. et al., J. Biomed. Mater. Res. 36: 125 (1997)). A stable non-toxic water soluble polyethylene glycol based polyvinyl alcohol (PEG-PVA) copolymer graft comprising 25% PEG and 75% PVA with the vinyl alcohol moieties grafted on a PEG backbone has been developed (Kollicoat IR, BASF). This copolymer is hydrophilic, highly flexible and is approved for use as a coating in tablets to modify drug release (Ali S., et al., Am. Pharm. Review 18:10 (2015). The utilization of PVA and PEG coatings on a coronary guidewire as an excipient to deliver medications to the vasculature has not been taught.

Polyvinyl acetate (PVAc) is a hydrophobic polymer which is useful in modifying the release of drugs from various hydrophilic polymers such as PVA and PVP (see, e.g., Ali, S., et al, Am Pharm Rev 18:2 (2015 May-June), Kolter, K., et al., Int. J. Pharm. 457: 407 (2013). PVAc is insoluble, non-toxic, and exhibits minimal swelling in aqueous solutions. It is widely used in the food industry as a base for chewing gum and for coating fruit and vegetables especially in Asia. PVAc has recently been investigated in the medical field to provide controlled release of various medications from pellets and tablets to optimize therapeutic efficacy and reduce side effects. PVAc is available as a 30% dispersion comprising Povidone K30 as a pore former and sodium lauryl sulfate as a wetting solution (Kollicoat SR 30 D, BASF) to improve the release profile from tablets. For example, the release of propranolol from a hydrophilic graft of PEG-PVA copolymer pellet was markedly delayed by increasing the ratio of PVAc to PEG-PVA. The utilization of PVAc in various concentrations to modify the release of drugs from hydrophilic polymers such as PVA on a guidewire for intervention procedures has not been reported.

In sum, despite the beneficial properties of hydrogels that comprise polymers such as PVA and PVAc, the incorporation of such hydrogels into coatings on medical devices such as guidewires that can deliver therapeutics has remained elusive. Thus, there remains a need for medical devices coated with hydrogels that can control drug-release rate. These needs and others are met herein.

SUMMARY

In accordance with the purpose(s) of the invention, as embodied and broadly described herein, the invention, in one embodiment, relates to hydrogel-coated devices having a therapeutic agent incorporated within the coating, and methods of making and using such devices in, for example, the treatment of vascular and/or organ damage.

Disclosed herein are medical devices comprising a coating of a hydrogel, wherein a therapeutic agent is incorporated within the coating, wherein the coating releases the therapeutic agent when in contact with a body fluid.

According to one embodiment, disclosed herein is a guide wire comprising: (a) a plurality of coils; (b) a primer layer attached to the plurality of coils covalently via silane coupling, the primer layer comprising methoxy-capped polyethylene glycol (PEG); and (c) a coating of a hydrogel attached to the primer layer via hydrogen bonds, the hydrogel comprising water and a polymer selected from polyvinyl alcohol (PVA), polyvinylpyrrolidone (PVP), polyvinyl acetate (PVAc), polyethylene glycol (PEG), poly(methyl acrylate), poly(ethyl acrylate), poly(methyl methacrylate), poly(acrylic acid), or a blend, combination, or copolymer thereof, wherein a therapeutic agent is incorporated within the coating, and wherein the coating releases the therapeutic agent when in contact with a body fluid.

According to a further embodiment, disclosed herein is a method for coating a guidewire comprising: (a) creating a plurality of hydroxyl groups on a surface of a non-coated guidewire comprising a plurality of coils; (b) reacting the non-coated guidewire with a methoxy-capped polyethylene glycol (PEG) to form a primer layer attached to the plurality of coils covalently via silane coupling; and (c) coating the guidewire comprising the primer layer with a solution, the solution comprising a therapeutic agent and a hydrogel comprising water and a polymer selected from polyvinyl alcohol (PVA), polyvinylpyrrolidone (PVP), polyvinyl acetate (PVAc), polyethylene glycol (PEG), poly(methyl acrylate), poly(ethyl acrylate), poly(methyl methacrylate), poly(acrylic acid), or a blend, combination, or copolymer thereof; thereby providing a hydrogel coating on the guidewire.

According to a further embodiment, disclosed herein is a kit comprising a disclosed guidewire, and one or more of: a medical device known for the treatment of vascular and/or organ damage; an agent known for the treatment of vascular and/or organ damage; an anesthetic agent; instructions for administering the disclosed guidewire; and instructions for treating vascular and/or organ damage.

While embodiments of the present invention can be described and claimed in a particular statutory class, such as the system statutory class, this is for convenience only and one of skill in the art will understand that each embodiment of the present invention can be described and claimed in any statutory class. Unless otherwise expressly stated, it is in no way intended that any method or embodiment set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

BRIEF DESCRIPTION OF DRAWINGS

The accompanying figures, which are incorporated in and constitute a part of this specification, illustrate several embodiments and together with the description serve to explain the principles of the invention.

FIG. 2 shows another representative guidewire with the same coil spacing over 15 cm but with a different tip design comprising approximately 30 mm of tight platinum-tungsten coils for radio-opacity. The surface area can be modified on either guidewire design by varying the coil space from 0.001 to 0.005 inches to adjust for the desired drug load required for optimal therapeutic efficacy.

In FIG. 10A, the radiopaque platinum-tungsten portion was incorporated in the mandrel and in FIG. 10B, it was in the 3-cm of tightly wound coil at the tip. FIG. 10C shows a micrograph of the redesigned 0.005-inch coils before coating. FIG. 10D is a micrograph of the 0.005-inch coils after coating with the PEG-silane primer layer, adenosine-loaded hydrogel layer and diffusion-barrier layer.

FIG. 17B shows the fold increase in CFV, which equates to coronary flow reserve (CFR). The CFR was greater than 2.0 for the first 15 minutes. The small spike in CFV when the guidewire was removed was likely due to an incremental surge in adenosine release due to wire manipulation. The adenosine-releasing wire did not affect mean blood pressure (MABP) or heart rate, as shown in FIGS. 17C and D, respectively. Values are means±SEM.

FIGS. 18A-C are coronary angiograms of circumflex in LAO projection. FIG. 18A: Baseline; FIG. 18B: Adenosine guidewire positioned in distal vessel with radio-opaque tip (solid arrow) clearly visible; FIG. 18C: Post wire removal after 30 mins showing normal flow. Also shown (dashed arrow) is the doppler Combowire used to measure coronary flow velocity.

FIGS. 20A-F are line graphs summarizing three experiments in which acetylcholine was infused into the coronary artery after the adenosine-loaded guidewire was inserted into the artery. Experiment one is summarized in FIGS. 20A-B; experiment two in FIGS. 20C-D; and experiment three in FIGS. 20E-F. Coronary flow velocities (CFV) are illustrated in FIGS. 20A, 20C, and 20E and associated mean arterial blood pressures (MABP) are shown in FIGS. 20B, 20D and 20F. In all three experiments, insertion of the adenosine-releasing guidewire immediately increased CFV and prevented acetylcholine from reducing CFV below baseline.

FIGS. 21A-D are line graphs summarizing two additional experiments in which acetylcholine was infused into the coronary artery after the adenosine-loaded guidewire was inserted into the artery. Experiment one is summarized in FIGS. 21A-B; and experiment two in FIGS. 21C-D. Coronary flow velocities (CFV) are illustrated in FIGS. 21A and 21C and associated mean arterial blood pressures (MABP) are shown in FIGS. 21B and 21D. In both experiments, insertion of the adenosine-releasing guidewire immediately increased CFV and prevented acetylcholine from reducing CFV below baseline. In FIG. 21C, removal of the adenosine-releasing guidewire while maintaining the intracoronary infusion of acetylcholine resulted in a rapid and profound decline in CFV.

FIGS. 22A-D are coronary angiograms showing an example of the "no-reflow" phenomenon (NRF) reversed by an adenosine-releasing guidewire. FIG. 22A: A baseline angiogram was obtained with the Combowire (dashed arrow) in the proximal LAD. FIG. 22B: Soon after administration of acetylcholine, severe NRF occurred with total cessation of blood flow in the proximal LAD (solid white arrow). FIG. 22C: Upon placement of an adenosine-releasing guidewire (solid black arrow) in the LAD, coronary flow was rapidly restored and maintained even while infusing acetylcholine for an additional 20 min. FIG. 22D: After stopping acetylcholine and removing the guidewire, a final angiogram showed that normal coronary flow was maintained.

FIGS. 24A-H show historical evolution from November 2018 to April 2020 of different coating formulations and applications and drug size modification to obtain a smooth coating surface with an optimal elution profile for a percutaneous coronary intervention (PCI) procedure. FIG. 24A: rapid release of adenosine with a single layer coating; FIG. 24B: development of a second barrier layer with low polymer mass; FIG. 24C: Utilization of PVAC in barrier coat with overall low polymer mass; FIG. 24D: employed new manual coating technique and increased polymer mass; FIG. 24E: Electronic coating machine used with varying ratios of PVAC with PVA in barrier layer; FIG. 24F: Jet milled adenosine was manufactured to reduce particle size and improve dispersion in hydrogel resulting in a smooth coating surface; FIG. 24G: Total polymer weight increased resulting in prolonged elution profile; FIG. 24H: Reduction in coating mass producing an ideal elution profile for PCI procedure.

FIGS. 25A-E show platelet aggregation studies. FIG. 25A: Representative platelet aggregation tracings showing aggregation responses to ADP (2 µM) collagen (1 µg/ml), ADP+Adenowire, collagen+Adenowire, ADP+Control wire and collagen+Control wire. Adenowires were coated with our novel hydrophilic coating that contained adenosine; Control wires were similarly coated but did not contain adenosine. Bar graphs summarize the effects of treatments on (FIG. 25B) area under the aggregation curve, (FIG. 25C) maximum aggregation, (FIG. 25D) slope of the aggregation curve and (FIG. 25E) the lag time between adding the agonist and onset of aggregation. Adenowires markedly inhibited platelet aggregation. The inert coating also manifested anti-platelet properties that was similar to, but not quite as efficacious as, Adenowires. *$P<0.05$ versus agonist without wire; †$P<0.05$ versus corresponding Control wire.

Figure 1:
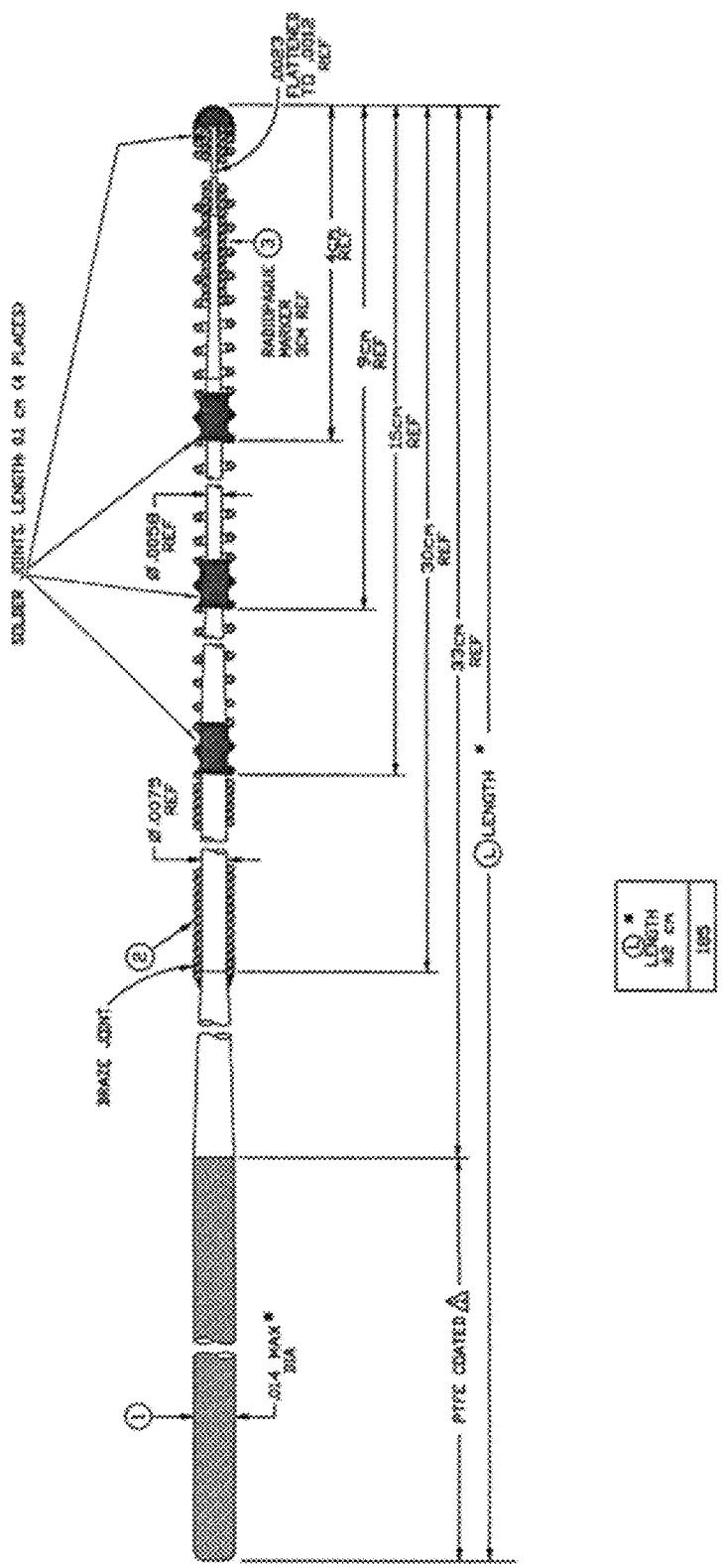
FIG. 1 shows a representative line diagram of a 0.014 inch stainless steel guidewire with the distal 15 cm having a coil spacing of 0.005 inches to accommodate the coating of a hydrophilic/drug polymer. The tip contains an additional platinum-tungsten rod attached to the mandrel to allow visualization during fluoroscopy
Figure 3:
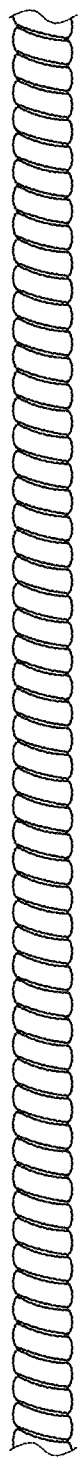
FIG. 3 shows a representative micrograph of a guidewire coated with PVA/PVP hydrogel containing adenosine. Note the coating is smooth and fills the entire coil spaces.
Figure 4:
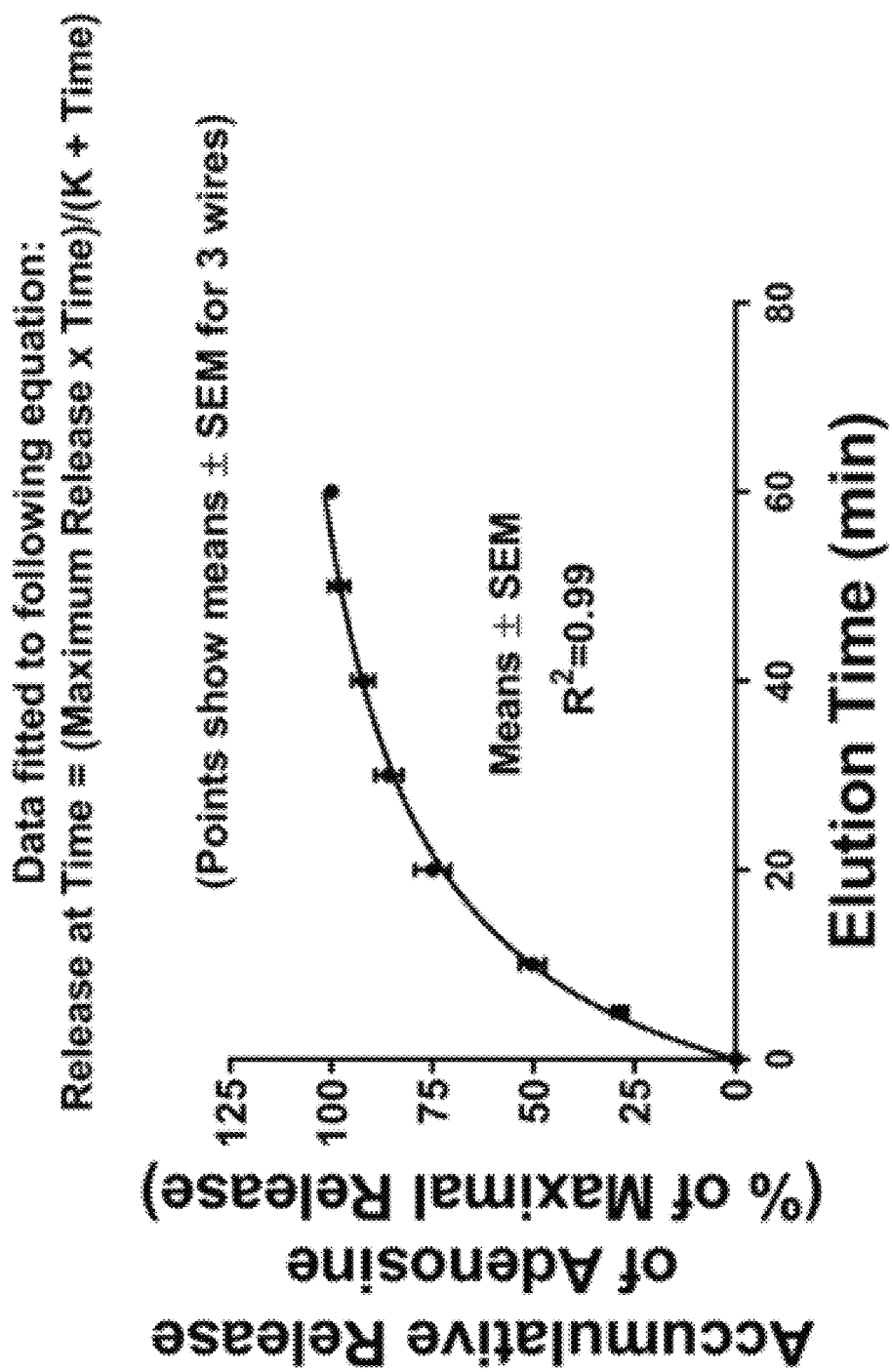
FIG. 4 illustrates representative time release of a therapeutic agent, adenosine, from the distal 10 cm of three guidewires with two coats of PVA/PVP polymer cured with 2 freeze/thaw cycles. The inner therapeutic coat was a 7.5% (w/w) of PVA/PVP with 1.5 mg of adenosine added as described in the application. The outer barrier layer was made of 10.0% (w/w) of PVA/PVP. The guidewire was placed in a beaker containing phosphate-buffered saline at 37° C. that was constantly stirred with a magnetic device. Samples were taken periodically from the beaker and analyzed for adenosine amount by UV spectrophotometry (absorption at 260 nm). Note the complete elution of the drug in a curvilinear fashion over 60 minutes.
Figure 5:
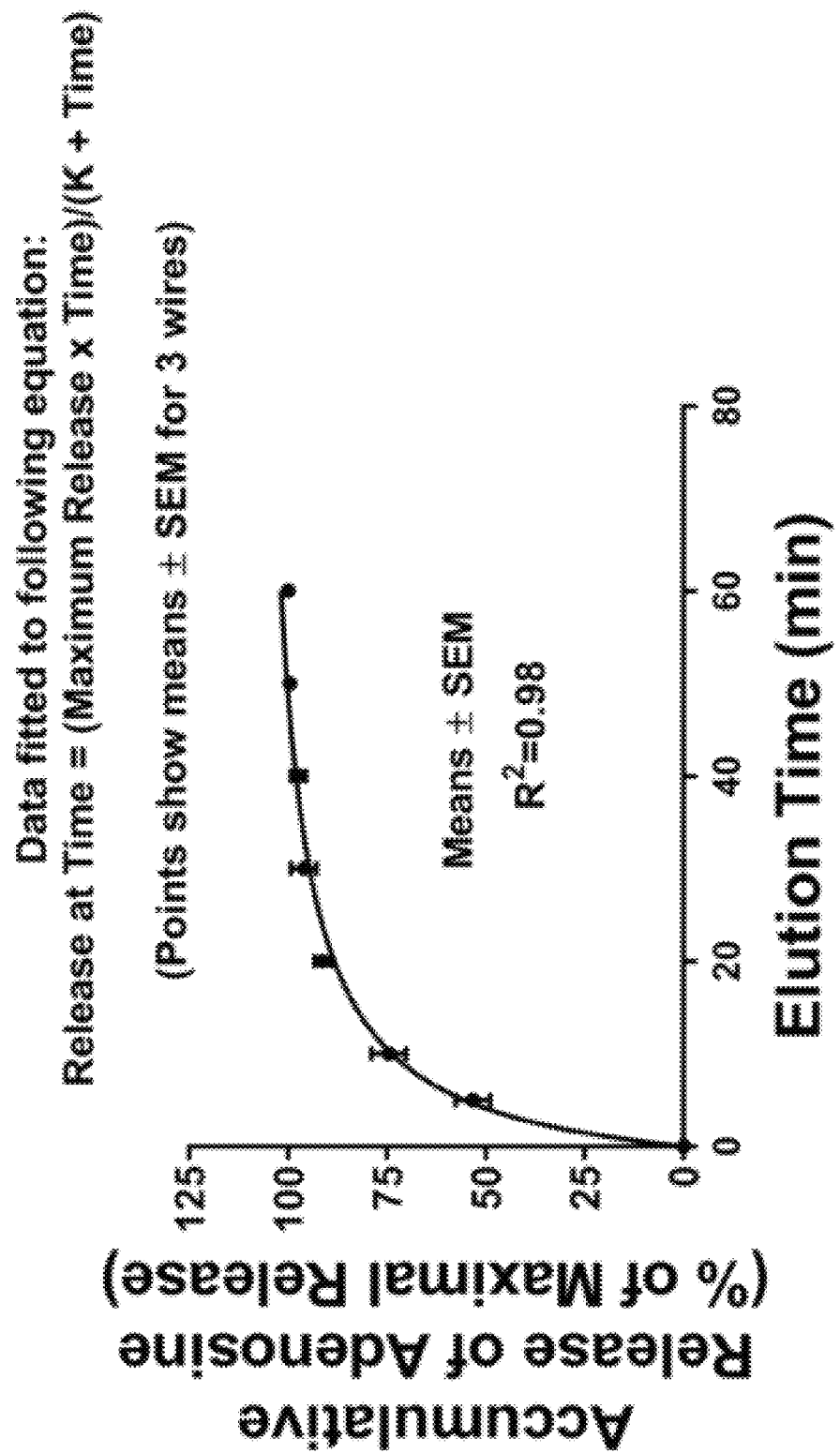
FIG. 5 demonstrates a representative elution profile of the sample drug, adenosine, by altering the number of freeze/thaw cycles (8) and polymer concentration (10% for inner and 15% for outer layer) and the mass of the barrier coat. Note that elution was more rapid with greater than 90% eluted over 20 minutes.
Figure 6:
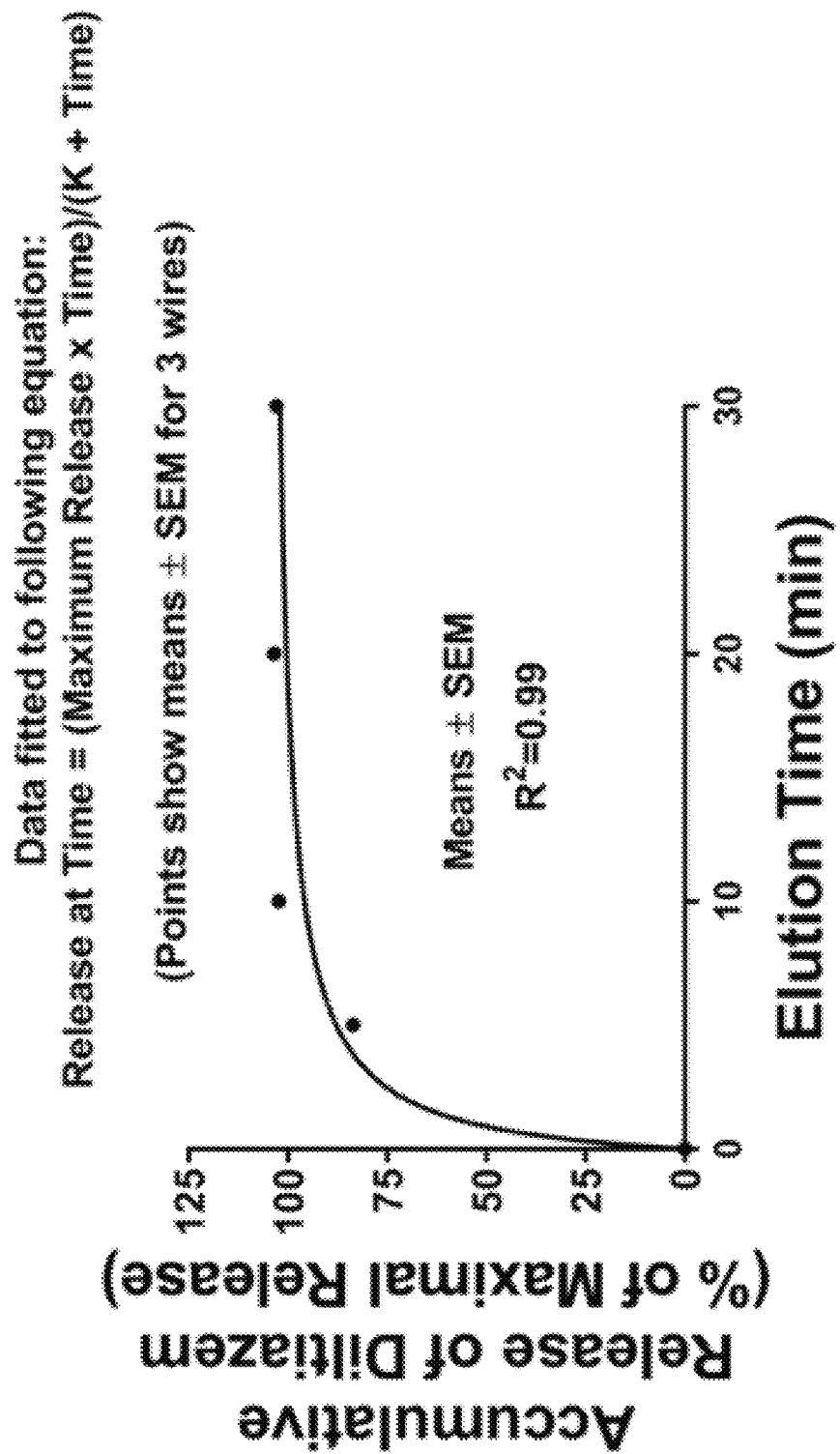
FIG. 6 illustrates a representative example of an extremely rapid elution of another drug diltiazem utilizing a polymer with a ratio of PVA/PVAC and two freeze/thaw cycles. The drug was completely eluted over 10 minutes.
Figure 7:
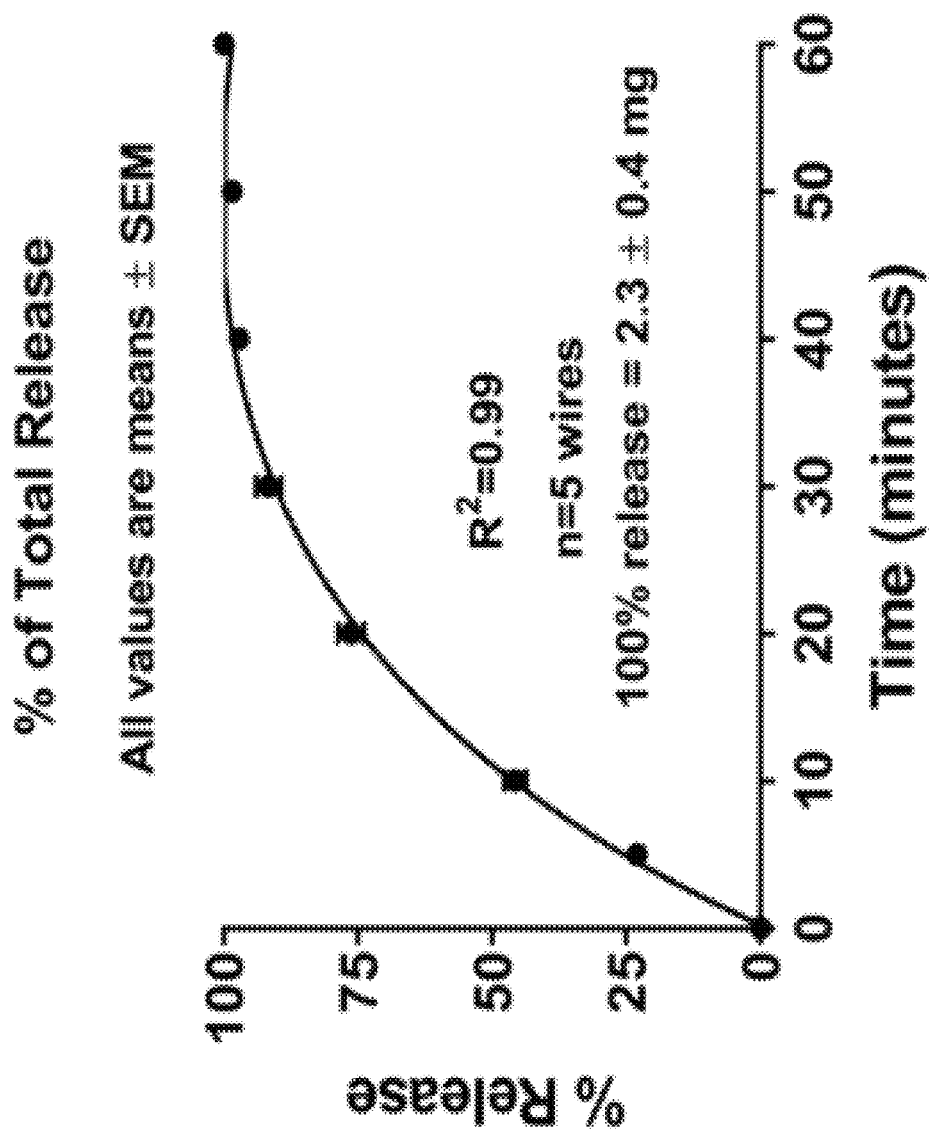
FIG. 7 shows representative adenosine release from guidewires coated with a polymer mixture containing a 3:1 and 1:1 ratios of PVAC to PVA. Note the release profile was optimal for a typical coronary interventional procedure.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting. Although any methods and materials similar or equivalent to those described herein can be used in the practice or testing of the present invention, example methods and materials are now described.

While embodiments of the present invention can be described and claimed in a particular statutory class, such as the system statutory class, this is for convenience only and one of skill in the art will understand that each embodiment of the present invention can be described and claimed in any statutory class. Unless otherwise expressly stated, it is in no way intended that any method or embodiment set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

In this specification and in the claims that follow, reference will be made to a number of terms, which shall be defined to have the following meanings:

Throughout the description and claims of this specific specification the word "comprise" and other forms of the word, such as "comprising" and "comprises," means including, but not limited to, and is not intended to exclude, for example, other additives, components, integers, or steps. In addition, as used in the specification and in the claims, the term "comprising" can also include the embodiments "consisting of" and "consisting essentially of."

As used in the description and appended claims, the singular forms "a," "an," and "the" include pleural references unless the context clearly dictates otherwise. Thus, for example, reference to "a composition" includes mixtures of two or more compositions.

"Optional" or "optionally" means that the subsequent described event or circumstance can or cannot occur, and that the description includes instances where the event or circumstance occurs and instances where it does not.

Ranges can be expressed herein as from "about" one particular value, and/or to "about" another particular value.

When such range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are number of values disclosed herein, and that each value is also herein disclosed as "about" that particular value in addition to the value itself. For example, if the value "10" is disclosed then "about 10" is also disclosed. It is also understood that when a value is disclosed, then "less than or equal to" the value, "greater than or equal to the value," and possible ranges between the values are also disclosed as appropriately understood by the skilled artisan. For example, if the value "10" is disclosed, then "less than or equal to 10" as well as "greater than or equal to 10" is also disclosed. It is also understood that throughout the application data are provided in a number of different formats and that data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used throughout, "subject" refers to an individual. Thus, the "subject can include domesticated animals, such as cats, dogs etc., livestock (e.g., cattle, horses, pigs, sheep, goats, etc.), laboratory animals (e.g., mouse, rabbit, rat, guinea pig, etc.) and birds. The term does not denote a particular age or sex. Thus, adult and newborn subjects, as well as fetuses, whether male or female, are intended to be covered. In one embodiment, the subject is a mammal, such as a primate or human. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various embodiments, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one embodiment, the subject is a mammal such as a primate, and, in a further embodiment, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compositions, devices, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various embodiments, a preparation can be administered therapeutically; that is, administered to treat an existing disease or condition. In further various embodiments, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various embodiments, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and singlestranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

By "pharmacologically acceptable" is meant a material that is not biologically or otherwise undesirable, i.e., the material can be administered to an individual along with the relevant active compound without causing clinically unacceptable biological effects or interacting in a deleterious manner with any of the other compounds on the pharmaceutical composition in which it is contained.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "guidewire," as described herein, refers to a device that crosses the target vessel lesion during a vascular interventional procedure.

The term "adenosine analogue," as described herein, refers to any chemical derivative of adenosine. Examples are listed in Table 1 of Chapter 6 (pages 104 through 107) by K. M Jacobson and A. M. Van Rhee in Purinergic Approaches in Experimental Therapeutics (edited by K. A. Jacobson and M. F Jarvis, Wiley-Liss, New York, 1977) and in Chapter 6 (pages 130-140) by K. A. Jacobson and L. J. S. Knutsen in Purinergic and Pyrimidinergic Signalling I; (editors M. P. Abbracchio and M. Williams, Springer, Berlin, 2001), which are hereby incorporated in their entirety for their teaching of adenosine analogs.

The term "receptor agonist," as described herein, refers to a chemical that binds to receptors either on cell surfaces or within cells and causes receptors to trigger a signal transduction process.

The term "therapeutic substance" refers to any substance that when administered to a subject appropriately at appropriate doses has a beneficial effect on the subject.

The term "release layer" refers to a layer that regulates the rate of release of a therapeutic agent. Two preferred release layers for use in accordance with the present invention are carrier layers and barrier layers.

The term "carrier layer" refers to a layer that contains a therapeutic agent and from which the therapeutic agent is released.

The term "barrier layer" refers to a layer that is disposed between a source of the therapeutic agent and a site of intended release and that impedes the rate at which the therapeutic agent is released.

Certain materials, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

A. MEDICAL DEVICES

Disclosed herein are medical devices coated with carrier and optional barrier layers of hydrophilic polymers that regulate the release of therapeutic agents, e.g., into the blood vessels during an interventional procedure.

Also disclosed are medical devices with coronary guidewires preferred with a portion coated with a hydrophilic polymer containing one or more therapeutic agents to improve acute and chronic outcomes during and after the interventional procedure.

Also disclosed are therapeutic agents, which are immersed in the hydrophilic coating allowing for controlled and continuous release of the therapeutic agent, e.g., into the vascular tree throughout an interventional procedure.

"Therapeutic agents," "pharmacologically active agents," "pharmacologic active materials," "drugs," and other terms may be used interchangeably and include generic and non-generic therapeutic agents. Therapeutic agents may be used singly or in combination.

Therapeutic agents may be generally classified as vasodilators, anti-inflammatory agents, anti-thrombotic, anti-platelet, anti-proliferative, anesthetic agents, vascular growth cell promoters and inhibitors and anti-lipemic agents.

Exemplary therapeutic agents are candidates for vascular treatment regimens include: Vasodilatory agents include a number of classes of agents that resulted in the reduced vasomotor tone in the large and small vessels thereby enhancing blood flow to the organs. Examples but not necessarily inclusive are: (a) cyclic nucleotide pathway agents such as adenosine, adenosine analogs, phosphodiesterase inhibitors, adenosine uptake inhibitors, inhibitors of adenosine kinase, inhibitors of adenosine deaminase; (b) calcium channel blockers including benzothiazepines such as diltiazem and clentiazem, dihydropyridines such as nifedipine, amlodipine and nicardapine and phenylalkylamines such as verapamil; (c) serotonin pathway modulators including: 5-HT antagonists such as ketanserin and naftidrofuryl as well as 5-HT uptake inhibitors such as fluoxetine; (d) catecholamine modulators including alpha-antagonists such as prazosin and bunazosine, beta-antagonists such as propranolol and alpha/beta antagonists such as labetalol and carvedilol; (e) endothelin receptor antagonists; (f) nitric oxide donors/releasing molecules including organic nitrates/nitrites such as nitroglycerin, isosorbide dinitrate and amyl nitrate, inorganic nitroso compounds such as sodium nitroprusside, synonymies such as molsidomine and linsidomine; (g) ACE inhibitors such as cilazapril, fosinopril and enalapril; (h) angiotensin receptor blockers (ARBs) such as losartan and candesartan; and (i) 17β-estradiol metabolites such as 2-methoxyestradiol and 2-hydroxyestradiol.

Anti-inflammatory agents can also be used. Examples of these include, but are not limited to, prednisone, dexamethasone, hydrocortisone, estradiol, 2-methoxyestradiol, 2-hydroxyestradiol, triamcinolone, mometasone, fluticasone, clobetasol, and nonsteroidal anti-inflammatories such as, for example, acetaminophen, ibuprofen, naproxen, adalimumab, and sulindac. Other examples of these agents including those that block cytokine activity or inhibit binding of cytokines or chemokines to the cognate receptors to inhibit pro-inflammatory signals transduced by cytokines or the chemokines. Representative examples of these agents include anti-interleukin, anti-MCP 1, anti-CCR2, anti-GM-CSF, and anti-TNF antibodies.

Anti-thrombotic agents that interfere in the coagulation pathway and thrombolytic agents that degrade thrombi can also be used. Examples of the former include heparin, heparin sulfate, and low molecular weight heparins such as for example the compound having the trademark Clivarin. Also included are direct thrombin inhibitors such as for example, melagatran, ximelagatran, argatroban, inogatran, and peptidimimetics of binding site of the Phe-Pro-Arg fibrinogen substrate for thrombin. Thrombolytic agents include but are not limited to urokinase or recombinant urokinase, pro-urokinase or recombinant pro-urokinase, tissue plasminogen activator or its recombinant form and streptokinase.

Also disclosed are anti-platelet agents act by inhibiting aggregation, adhesion or activation. Examples, but not limited, include aspirin, and thiopyrimidine (ticlopidine, clopidogrel) and GP IIb/IIIa inhibitors such as abciximab, eptifibatide and tirofiban and anti-P-selectin antibodies, anti-E-selectin antibodies that block P-selectin or E-selectin binding to their respective Also disclosed are anti-proliferative/anti-mitotic agents such as as 2-methoxyestradiol, 2-hydroxyestradiol, paclitaxel, 5-fluorouracil, cisplatin, vinblastine, vincristine, epothilones, angiostatin, angiopeptin, monoclonal antibodies capable of blocking smooth muscle proliferation, and thymidine kinase inhibitors.

Also disclosed are anesthetic agents such as lidocaine and bupivacaine and ropivacaine.

Vascular cell growth promoters and inhibitors include growth factors promoters such as growth factors, transcriptional activators, and translational promoters. Vascular cell growth inhibitors such as growth factor inhibitors, growth factor receptor antagonists, translational repressors, transcriptional repressors, replication inhibitors, inhibitory antibodies, and antibodies directed against growth factors.

Other agents that can be used in combination with the compounds of this intervention include anti-lipemic agents such as for example fenofibrate, atorvastatin, fluvastatin, lovastatin, mevastatin, pitavastatin, pravastatin, rosuvastatin, and simvastatin.

Also disclosed is that a drug can be used in combination with one or two other therapeutic agents.

In some aspects, the therapeutic agent can have a suitable particle size for incorporation into the hydrogel carrier layer. For example, the therapeutic agent can have an average particle size of less than about 10 microns. In a further aspect, the therapeutic agent can have an average particle size of less than about 5 microns. Commercially-available therapeutic agents, e.g., adenosine, can be reduced in size by techniques known in the art such as jet-milling. In one aspect, when the therapeutic agent comprises adenosine, the adenosine can be jet-milled to an average particle size of less than about 10 microns, e.g., less than about 5 microns.

Also disclosed are hydrophilic coatings in which the therapeutic agent can be dispersed and which results in the controlled release of the drugs throughout interventional procedure.

Also disclosed is a rapid elution profile resulting in at least 75% release of the therapeutic agents by modulation of the carrier and/or barrier layers of the coating.

In various embodiments, the hydrogel for the coating is a blend of PVA and PVP of varying molecular weights, concentrations and proportions, which results in network stability and drug elution.

Also disclosed is a method for improvement in drug dispersion in the hydrogel via manufacture of nanoparticles of the pharmacological agent or incorporation as "caged" molecules, e.g., caged in cyclodextrins, for example CAPTISOL.

Also disclosed are techniques to disperse medications in the hydrogel and apply the suspension to the medical device. Examples include dip coating, spin coating, solvent spraying, ink jet techniques, electrostatic techniques or combinations of the processes. Where appropriate they can be repeated or combined to build up a release and/or barrier layer to a desired thickness.

Also disclosed is a guidewire design with a sufficient surface area which allows accommodation of adequate amounts of coating impregnated with a pharmacologically active agent to reduce acute and chronic complications of interventional procedures.

In various embodiments, the medical device, e.g., guidewire, comprises a coating of a hydrogel, wherein a therapeutic agent is incorporated within the coating, and wherein the coating releases the therapeutic agent when in contact with a body fluid. The medical device can comprise a single hydrogel coating containing the therapeutic agent or alternatively can comprise multiple hydrogel coatings. In some embodiments, one or more outer diffusive barrier layers can be applied to the hydrogel-coated medical device to further modulate the release of the therapeutic agent into the body.

In various embodiments, the medical device comprises a coating of a hydrogel, wherein the hydrogel comprises water and a polymer selected from polyvinyl alcohol (PVA), polyvinylpyrrolidone (PVP), polyvinyl acetate (PVAc), polyethylene glycol (PEG), poly(methyl acrylate), poly (ethyl acrylate), poly(methyl methacrylate), poly(acrylic acid), or a blend, combination, or copolymer thereof. In a further embodiment, the hydrogel coating comprises PVA and PVP.

According to one embodiment, the medical device comprises an outer diffusive barrier layer over the hydrogel coating that contains the therapeutic agent. In one embodiment, the outer diffusive barrier layer comprises PVA, PVAc, PVP, PEG, or a blend, combination, or copolymer thereof. In a further embodiment, the outer diffusive barrier layer comprises a PVA-PEG copolymer blended with PVAc.

In various embodiments, the hydrogel comprises a polyacrylate. Examples of polyacrylates include, but are not limited to, poly(methyl acrylate), poly(ethyl acrylate), poly (methyl methacrylate), poly(acrylic acid), and blends, combinations, and copolymers thereof.

In various embodiments, the medical device is a guidewire. In a further embodiment, the guidewire comprises a distal end that is wrapped with a plurality of coils having spaces in-between the coils, and wherein the coating is present at least in the spacing between the coils. In a further embodiment, the coating can be present in the spacing between the coils and on the coils themselves.

In a further embodiment, the spaces are of from about 0.014 mm (0.0006 inches) to about 0.123 mm (0.0048 inches). Thus, in various embodiments, the spaces are of from about 0.014 mm to about 0.12 mm, about 0.014 mm to about 0.10 mm, about 0.014 mm to about 0.075 mm, about 0.014 mm to about 0.05 mm, about 0.014 mm to about 0.25 mm, about 0.01 mm to about 0.123 mm, about 0.025 mm to about 0.123 mm, about 0.05 mm to about 0.123 mm, about 0.075 mm to about 0.123 mm, or about 0.1 mm to about 0.123 mm.

In a further embodiment, the medical device has a surface area of from about 0.021 square inches to about 0.500 square inches. In a further embodiment, the medical device has a surface area of from about 0.021 square inches to about 0.172 square inches. Thus, in various embodiments, the medical device has a surface area of from about 0.021 square inches to about 0.17 square inches, about 0.021 square inches to about 0.15 square inches, about 0.021 square inches to about 0.1 square inches, about 0.021 square inches to about 0.075 square inches, about 0.021 square inches to about 0.05 square inches, about 0.05 square inches to about 0.172 square inches, about 0.075 square inches to about 0.172 square inches, about 0.1 square inches to about 0.172 square inches, about 0.125 square inches to about 0.172 square inches, or about 0.15 square inches to about 0.172 square inches.

In various embodiments, the medical device comprises a plurality of silanols and the hydrogel is attached to the silanols via hydrogen bonds. In a further embodiment, the therapeutic agent is dissolved or dispersed in the hydrogel that is attached to the silanols via hydrogen bonds.

In various embodiment, the therapeutic agent dilates a plurality of blood vessels. In a further embodiment, the therapeutic agent is a calcium-channel blocker. In a further embodiment, the therapeutic agent inhibits platelet aggregation. In addition to the therapeutic agent, the hydrogel coating can further inhibit platelet aggregation in some embodiments. In a still further embodiment, the therapeutic agent is an adenosine receptor agonist. In yet a further embodiment, the therapeutic agent is adenosine or an adenosine analog. In an even further embodiment, the therapeutic agent is diltiazem. In a still further aspect, the therapeutic agent is dissolved within the hydrogel.

The therapeutic agent present in the hydrogel coating can have a variety of particle sizes. According to one embodiment, the therapeutic agent is a nanoparticle or a microparticle. In a further embodiment, the therapeutic agent has an average particle size of less than about 10 microns. In a still further embodiment, the therapeutic agent has an average particle size of less than about 5 microns.

In various embodiments, the coating releases the therapeutic agent immediately upon contact with the body fluid. In a further embodiment, the coating releases the therapeutic agent gradually.

In a further embodiment, the coating releases a therapeutic amount of the therapeutic agent over a time period of from about 0.5 minutes to about 120 minutes. In a further embodiment, the coating releases a therapeutic amount of the therapeutic agent over a time period of from about 10 minutes to about 120 minutes. Thus, in various embodiments, the coating releases the therapeutic agent over a time period of from about 10 minutes to about 100 minutes, about 10 minutes to about 75 minutes, about 10 minutes to about 50 minutes, about 10 minutes to about 25 minutes, about 25 minutes to about 120 minutes, about 50 minutes to about 120 minutes, about 75 minutes to about 120 minutes, or about 100 minutes to about 120 minutes.

In a further embodiment, the coating releases the therapeutic agent at a rate of from about 20 mcg/min to about 1,000 mcg/min. In a further embodiment, the coating releases the therapeutic agent at a rate of from about 20 mcg/min to about about 200 mcg/min. Thus, in various embodiments, the coating releases the therapeutic agent at a rate of from about 20 mcg/min to about 175 mcg/min, about 20 mcg/min to about 150 mcg/min, about 20 mcg/min to about 125 mcg/min, about 20 mcg/min to about 100 mcg/min, about 20 mcg/min to about 75 mcg/min, about 20 mcg/min to about 50 mcg/min, about 50 mcg/min to about 175 mcg/min, about 75 mcg/min to about 175 mcg/min, about 100 mcg/min to about 175 mcg/min, about 125 mcg/min to about 175 mcg/min, or about 150 mcg/min to about 175 mcg/min.

Examples of body fluid include, but are not limited to, blood, plasma, urine, cerebral spinal fluid, plasma exudate, gastric fluid, intestinal fluid, pericardial fluid, and interstitial fluid.

In various embodiments, the medical device further comprises more than one therapeutic agent, e.g., two or more. The therapeutic agents can be different and both incorporated within the hydrogel coating.

In one exemplary embodiment, the medical device is a guidewire having a distal end that is wrapped with a plurality of coils having spaces in between the coils. The hydrogel coating, e.g., a PVA/PVP coating, can be coated at least in the spaces between the coils and in some embodiments on the coils themselves. A therapeutic agent such as adenosine among others can be incorporated within the hydrogel coating, e.g., the PVA/PVP coating. In some embodiments, the guidewire can further comprise an outer diffusive barrier layer, e.g., a barrier layer comprising PVA and PVAc

B. METHODS FOR MAKING A MEDICAL DEVICE

Disclosed are methods for making a disclosed medical device, the method comprising: (a) creating a plurality of hydroxyl groups on a surface of a non-coated medical device; (b) reacting the non-coated medical device with a silylating agent; and (c) coating the non-coated medical device with a solution to form a hydrogel-coated medical device, wherein the solution comprises the hydrogel and the therapeutic agent, thereby making the disclosed medical device.

The method can be used to create a medical device such as a guidewire that has a single hydrogel coating layer or alternatively a medical device, e.g., guidewire, In a further embodiment, after application of the hydrogel coating that contains the therapeutic agent, the medical device can be further coated with an outer diffusive barrier layer over the hydrogel coating. In one embodiment, the outer diffusive barrier layer comprises PVA, PVAc, PVP, PEG, or a blend, combination, or copolymer thereof. In a further embodiment, the outer diffusive barrier layer comprises a PVA-PEG copolymer blended with PVAc. In a further embodiment, the outer diffusive barrier layer comprises PVA and PVAc, e.g., in a 1:3 ratio. The barrier solution used to form the outer layer can comprise PVA, PVAc, PVP, PEG, or a blend, combination, or copolymer thereof. According to one embodiment, the barrier solution comprises from about 1% to about 10% PVA and from about 5% to about 20% PVAc, based on the total weight of the barrier solution. In a further embodiment, the barrier solution can comprise a PVA-PEG copolymer blended with PVAc.

In various embodiments, creating the plurality of hydroxyl groups on the surface of the medical device is via oxygen plasma treatment or acid treatment.

In various embodiments, the silylating agent is methoxy-capped polyethylene glycol (PEG).

In one embodiment, the solution for forming the hydrogel-coated medical device comprises water and a polymer selected from polyvinyl alcohol (PVA), polyvinylpyrrolidone (PVP), polyvinyl acetate (PVAc), polyethylene glycol (PEG), poly(methyl acrylate), poly(ethyl acrylate), poly(methyl methacrylate), poly(acrylic acid), or a blend, combination, or copolymer thereof. In a further embodiment, the solution for forming the hydrogel-coated medical device comprises water and a combination of PVA and PVP, e.g., a 99:1 ratio of PVA:PVP.

In a further embodiment, the solution comprises the polymer (e.g., PVA) in an amount of from about 7.0% w/w to about 30% w/w, based on the total weight of the solution. In a further embodiment, the solution comprises the polymer (e.g., PVA) in an amount of from about 7.0% w/w to about 15% w/w, based on the total weight of the solution. Thus, in various embodiments, the solution comprises the polymer (e.g., PVA) in an amount of from about 7.0% w/w to about 12% w/w, about 7.0% w/w to about 10% w/w, about 7.0% w/w to about 9.0% w/w, about 9.0% w/w to about 15% w/w, about 10% w/w to about 15% w/w, or about 12% w/w to about 15% w/w. In one embodiment, the solution comprises from about 7.0% by weight to about 30% by weight of PVA. In a further embodiment, the solution comprising from about 7.0% by weight to about 30% by weight of PVA further comprises PVP in an amount ranging from about 0% to about 15% by weight, based on the total weight of the solution.

In a further embodiment, the solution comprises PVAc in an amount of from about 0% w/w to about 15% w/w. Thus, in various embodiments, the solution comprises PVAc in an amount of from about 0% w/w to about 12% w/w, about 0% w/w to about 10% w/w, about 0% w/w to about 8% w/w, about 0% w/w to about 6% w/w, about 0% w/w to about 4% w/w, about 0% w/w to about 2% w/w, about 2% w/w to about 15% w/w, about 4% w/w to about 15% w/w, about 6% w/w to about 15% w/w, about 8% w/w to about 15% w/w, about 10% w/w to about 15% w/w, or about 12% w/w to about 15% w/w.

In a further embodiment, the solution comprises PVP in an amount of from about 0% to about 15% by weight, based on the total weight of the solution. In a further embodiment, the solution comprises PVP in an amount ranging from about 0.07% w/w to about 0.15% w/w, based on the total weight of the solution. Thus, in various embodiments, the solution comprises PVP in an amount of from about 0.07% w/w to about 0.12% w/w, about 0.07% w/w to about 0.1% w/w, about 0.1% w/w to about 0.15% w/w, or about 0.12% w/w to about 0.15% w/w, based on the total weight of the solution.

In a further embodiment, the solution comprises the therapeutic agent in an amount of from about 0.1% about 30% by weight, based on the total weight of the solution. In a further embodiment, the solution comprises the therapeutic agent in an amount ranging from about 7.0% w/w to about 20% w/w, based on the total weight of the solution. Thus, in various embodiments, the solution comprises the therapeutic agent in an amount of from about 7.0% w/w to about 15% w/w, about 7.0% w/w to about 12% w/w, about 7.0% w/w to about 10% w/w, about 10% w/w to about 20% w/w, about 12% w/w to about 20% w/w, or about 15% w/w to about 20% w/w. In some embodiments, the solution can comprise two or more therapeutic agents that can be different, as described above.

C. METHODS FOR TREATING VASCULAR AND/OR ORGAN DAMAGE

The present intervention also relates to methods and compositions for reducing and preventing vascular and organ damage and improving outcomes during various vascular interventional procedures. For example, the present intervention relates to methods and compositions for reducing, preventing, or reversing vascular and organ damage and improving outcomes during vascular intervention procedures on various organs utilizing a drug delivery guidewire designed to attenuate deleterious acute and chronic events by rapidly releasing one or more medications into the downstream microcirculation during all or part of the interventional procedure. The concept of this intervention is to coat the guidewire in such a manner as to release one or more medications immediately following contact with blood in the vascular component compartment. The medication(s) can be incorporated into the distal end of the guidewire resulting in an immediate continual and concentrated release of the medications into the vascular tree distal to the culprit lesion being treated with mechanical intervention. Thus, the vascular bed can be prophylactically medicated prior to the performance of mechanical procedure. The high concentration of the medicant(s) in the distal bed prevents or reverses damages to the vascular tree induced by the release of embolic debris and/or humoral mediators following disruption of the atheromatous plaque by the mechanical intervention. Because by definition the guidewire is the first device that crosses the vascular lesion, the medications will immediately influence the distal vasculature to improve outcomes. The present intervention accomplishes direct intra-arterial administration of medications without the need for further injections of drugs by the physician and without the need for any additional manipulations. The medication can be automatically released from the tip of the guidewire without need for additional considerations by the physician. For example, the medication(s) can be released upon contact with water within the body fluids of a subject. Also, because the medication(s) is (are) released directly into the disease vascular bed, high concentrations are achievable compared with systemic administration. Furthermore, adverse effects due to systemic administration of the medications can be reduced or completely negated.

Thus, disclosed are methods for treating vascular and/or organ damage in a subject, the method comprising inserting into the subject's artery, vein, or cardiac chamber, a disclosed medical device. In further embodiments, treating is reducing, preventing, or reversing.

In a further embodiment, the medical device is inserted into the subject for a time period of less than 2 hours. Thus, in various embodiments, the medical device is inserted into the subject for a time period of less than 1.5 hours, less than 1 hour, or less than less than 0.5 hours.

In a further embodiment, the subject was previously diagnosed as having a need for a percutaneous coronary intervention. Examples of percutaneous coronary interventions include, but are not limited to, percutaneous balloon angioplasty, laser angioplasty, stent implantation, and atherectomy.

In all embodiments, the drug delivery guidewire can be used in vessel interventional procedures involving arteries and blood vessels supplying blood to the heart, brain, kidneys or peripheral circulation, both native arteries and blood vessels as well as saphenous vein, internal mammary artery and radial artery bypass vessels.

In all embodiments, the drug delivery guidewire can be used in a variety of vascular interventional procedures including percutaneous balloon angioplasty, laser angioplasty, stent (bare metal or drug-eluting) implantation and atherectomy. In all embodiments, the guidewire can be used in conjunction with a number of other devices including rotablator devices, protection devices, clot removal devices, and proximal and distal occlusion devices.

The guidewire can be designed to release therapeutic medication(s) beginning immediately after insertion and continuing throughout the duration of the procedure using a number of approaches including, but not limited to, incorporation of the medication(s) in a polymer from which the medication is released when in contact with body fluids. For example, the medication is immersed in the polymer and released when in contact with body fluids. The examples below illustrate the concept but are non-limiting. Numerous variations of this concept are possible, and the current invention incorporates all variations of this approach including other methods to release the medications and other medications.

D. KITS

Disclosed are kits comprising a disclosed medical device, and one or more of: (a) a medical device known for the treatment of vascular and/or organ damage; (b) an agent known for the treatment of vascular and/or organ damage; (c) an anesthetic agent; (d) instructions for administering a disclosed medical device; and (e) instructions for treating vascular and/or organ damage.

In various aspects, the informational material can be descriptive, instructional, marketing or other material that relates to the methods described herein and/or to the use of the devices for the methods described herein. For example, the informational material may relate to the use of the devices herein to treat a subject who has a need for, or who is at risk for developing a need for, a percutaneous coronary intervention.

In various aspects, the informational material can include instructions for administering the therapeutic agent incorporated within the coating of the device in a suitable manner to treat a human, e.g., in a suitable dose, dosage form, or mode of administration (e.g., a dose, dosage form, or mode of administration described herein). In a further aspect, the informational material can include instructions to administer the therapeutic agent to a suitable subject, e.g., a human having a need for, or at risk for developing a need for, percutaneous coronary intervention.

Examples of medical devices known for the treatment of vascular and/or organ damage include, but are not limited to, rotoblader devices, clot protection devices, clot removal devices, proximal occlusion devices, and distal occlusion devices.

Examples of agents known for the treatment of vascular and/or organ damage include, but are not limited to, cyclic nucleotide pathway agents, calcium channel blockers, serotonin pathway modulators, catecholamine modulators, endothelin receptor antagonists, nitric oxide donor or releasing agents, ACE inhibitors, angiotensin receptor blockers, anti-inflammatory agents, anti-thrombotic agents, anti-platelet agents, anti-proliferative or anti-mitotic agents, vascular cell growth promotors or inhibitors, and anti-lipemic agents.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

a. Raw Materials

TABLE 1

| Generic Name | Trade Name | Supplier | Catalog Number |
| --- | --- | --- | --- |
| PVA | MOWIOL28-99 (Ph Eur, JPE grade) Mw~145 kDa | EMD Millipore | 1413561000 |
| PVAc | KOLLICOAT SR 30 D | Sigma-Aldrich | 96329-500g |
| PVP | Povidone K-30 (USP grade) | Spectrum Chemical | P1454 |
| PEG-Silane | Methoxy PEG Silane | JenKem | n/a |
| Adenosine | Adenosine | Sigma-Aldrich | A9251 |
| Acetic acid | Acetic acid (glacial, >99.7%) | Sigma Aldrich | 695092-500ml |

PVA: polyvinyl alcohol; PVP: polyvinylpyrrolidone; mPEG: methoxy-capped polyethylene glycol.

b. Example 1

Stainless steel guidewires with 0.014 inch diameter and coil spacing of 0.005 inches in the distal 15 cm were cleaned with an ultrasonic probe for 5 min in ethanol, followed by deionized (DI) water for 5 min, and then dried via $N_2$ gas line.

The cleaned guidewires were then subjected to oxygen plasma treatment (see Reaction 1). A custom-made plasma oxygenator was utilized that produced a 1 $W/cm^2$ output connected to an oxygen tank whose regulator was set to a 1 L/min flow rate. The wires were exposed for 6 min. It should be noted that other methods for creating surface hydroxyl groups, such as acid treatments, can be substituted for plasma treatment.

Thirty minutes prior to the above reaction plasma treatment, m-PEG-silane (20 kDa MW) was dissolved at a concentration of 40 mg/ml in an ethanol/water solution (95:5 w/w) and titrated to pH 5.0 with glacial acetic acid. A 30 min dissolution time allows the m-PEG-silane to hydrolyze (see Reaction 2). It should be noted that other concentrations on m-PEG-silane in the range of 5-50 mg/ml and other molecular weights (1 to 20 kDa) can be substituted.

After plasma treatment, the wires were dipped in the PEG-silane solution and allowed to react for 2 hrs. Other reaction times in the range of 5 min to 5 hrs can be substituted. After 2 hrs, the wires were cured at 110° C. for 30 min in a vacuum oven set to maximum vacuum of less than 0.1 bar. These wires were then PEG-silane coated (see Reaction 3) and ready for drug/hydrogel coating. Other heating temperatures and durations can be used.

The polymer/drug coating was prepared as follows. A 20% (w/w) of a PVA/PVP (99:1 ratio) gel in DI water was created via heating and stirring to yield a supersaturated solution which was homogenous and free of bubbles. This gel was used to dilute further for desired coating concentrations.

Adenosine was employed as a sample therapeutic agent. A "drug coating" solution was created by diluting the above stock PVA/PVP solution with DI water and dry adenosine to create a 10% PVA/PVP (99:1) gel with 10% w/w adenosine (both dissolved and dry API distributed throughout the gel in a saturated solution). Mechanical distribution at 60° C. was used to achieve an evenly distributed and mixed gel. Other concentrations of adenosine can be used depending on the desired drug loading. Here it was desired to coat the desired guidewire length with 1.5 mg total adenosine over 10 cm of wire. It should be noted that other concentrations (7.5-15%) and other molecular weights of the polymers can be substituted.

A "diffusive layer" solution was created by diluting the above stock PVA/PVP solution with DI water to create a 12.5% PVA/PVP (99:1) gel. Other polymer solutions can be substituted, and range from 7.5-15% w/w.

PEG-silane treated wires were coated with a "drug coating" gel consisting of 10% adenosine and 10% PVA/PVP by running wires through a syringe barrel containing the "drug coating" solution at 60° C. The draw of the wire through the solution deposited the gel on the wire. The wire was immediately flash frozen by dipping the wire in liquid nitrogen, and then immediately placed in a freezer for 3 hrs. Following 3 hrs, the wire was left out at room temperature to thaw for 1 hr. This constitutes 1 "freeze-thaw" cycle. Other freezing and thawing times can be substituted for convenience, with freezing times generally ranging from 1 to 24 hrs, and thawing times from 30 min to 2 hrs. The above wire was subjected to 2 freeze-thaw cycles to induce crystallinity in the gel coating. Other freeze-thaw cycles can be substituted, and should be a minimum of 2. The wire with the deposited the "drug coating" layer were then coated with a "diffusive layer" by the coating, substituting the "drug coating" solution with the "diffusive layer" solution without adenosine. Multiple coatings of either layer can be added for increased drug loading or diffusive coatings for extended release.

c. Example 2

The drug elution profile can be significantly altered by changing the hydrogel concentrations, blend, molecular weight and the number of freeze/thaw cycles. Utilizing the same protocol as Example 1, the freeze/thaw cycles were increased to 3-8 and the barrier concentration was increased to 15.0% (w/w). Utilizing adenosine as the prototype therapeutic agent the elution profile was increased with the majority of drug elution occurring in 30 min.

d. Example 3

Cardizem-eluting wires were prepared similarly to adenosine-eluting wires. Briefly, stainless steel guidewires were plasma treated and cured as in Example 1. Using a concentrated stock solution of 20% (w/w) PVA/PVP (99:1 ratio), a "drug coating" solution of 7.5% PVA/PVP, 10% (w/w) dry Cardizem, and the remainder water was created. Heating to 60° C. and mechanical distribution was used to achieve a homogeneous solution. Other concentrations of Cardizem can be used to achieve the desired drug coating. It should be noted that other PVA/PVP concentrations (7.5-15%) and other molecular weights of the polymer can be substituted.

A "diffusive layer" solution, as in Example 1, was created using the same stock PVA/PVP solution and DI water to create a 12.5% PVA/PVP (99:1) gel. Other polymer solutions can be substituted, and range from 7.5-15% w/w.

PEG-silane treated wires were coated with a "drug coating" gel consisting of 10% Cardizem and 7.5% PVA/PVP by running wires through a syringe barrel containing the "drug coating" solution at 60° C. The draw of the wire through the solution deposited the gel on the wire. The wire was immediately flash frozen by dipping the wire in liquid nitrogen, and then immediately placed in a freezer for 3 hrs. Following 3 hrs, the wire was left out at room temperature to thaw for 1 hr. This constitutes 1 "freeze-thaw" cycle.

Other freezing and thawing times can be substituted for convenience, with freezing times generally ranging from 1 to 24 hrs, and thawing times from 30 min to 2 hrs. The wire in this example was subjected to 2 freeze-thaw cycles to induce crystallinity in the drug-coating layer. Other freeze-thaw cycles can be substituted, and should be a minimum of 2. The wire with the deposited "drug coating" layer was then coated with a "barrier layer" by substituting the "drug coating" solution with the "diffusive layer" solution without Cardizem. This coating was again flash-frozen using liquid nitrogen, and subject to 2 freeze-thaw cycles. Multiple coatings of either layer can be added for increased drug loading or diffusive coatings for extended release.

e. Example 4

Adenosine-eluting wires containing PVAc were made similarly to those with PVA/PVP alone, as in Example 1. Briefly, stainless steel guidewires were plasma treated and cured as in Example 1. A "drug coating" solution consisting of 17% total polymer in a 1:1 ratio of PVAc to PVA/PVP (8.5% PVAc, 8.5% PVA/PVP at a 99:1 ratio) was prepared by mixing commercial PVAc (Kollicoat® SR 30 D), packaged as a 30% dispersion with stabilizers and excipients, with the previously prepared 20% w/w PVA/PVP solution, powdered adenosine (10% w/w), and the remainder water. Heating to 60° C. and mechanical mixing was used to achieve a homogeneous solution. Other concentrations of Adenosine can be used to achieve the desired drug coating. It should be noted that other total polymer concentrations (10-20%), ratios of PVA to PVAc, and other molecular weights of the polymer can be substituted. Brand-name Kollicoat® can also be substituted with solutions prepared from powdered PVAc, using stabilizers such as sodium lauryl sulfate or sodium dodecyl sulfate to increase PVAc solubility.

A "barrier coating" solution consisting of 20% total polymer in a 1:1 ratio of PVAc to PVA/PVP (10% PVAc, 10% PVA/PVP at a 99:1 ratio) was prepared by mixing commercial PVAc (KOLLICOAT SR 30 D) with the previously prepared 20% w/w PVA/PVP solution and the remainder water. Heating to 60° C. and mechanical mixing was used to achieve a homogeneous solution.

PEG-silane treated wires were coated with a "drug coating" solution consisting of 10% adenosine and 17% PVAc/PVA/PVP by running wires through a syringe barrel containing the "drug coating" solution at 60° C. The draw of the wire through the solution deposited the gel on the wire. The wire was immediately flash frozen by dipping the wire in liquid nitrogen, and then immediately placed in a freezer for 3 hrs. Following 3 hrs, the wire was left out at room temperature to thaw for 1 hr. This constitutes 1 "freeze-thaw" cycle. Other freezing and thawing times can be substituted for convenience, with freezing times generally ranging from 1 to 24 hrs, and thawing times from 30 min to 2 hrs. The above wire was subjected to 2 freeze-thaw cycles to induce crystallinity in the gel layer. Other freeze-thaw cycles can be substituted, and should be a minimum of 2. The wire with the deposited "drug coating" layer was then coated with a "barrier layer" by substituting the "drug coating" solution with the "diffusive layer" solution without Adenosine. This coating was again flash-frozen using liquid nitrogen, and subject to 2 freeze-thaw cycles. Multiple coatings of either layer can be added for increased drug loading or diffusive coatings for extended release.

f. Example 5

Figure 8:
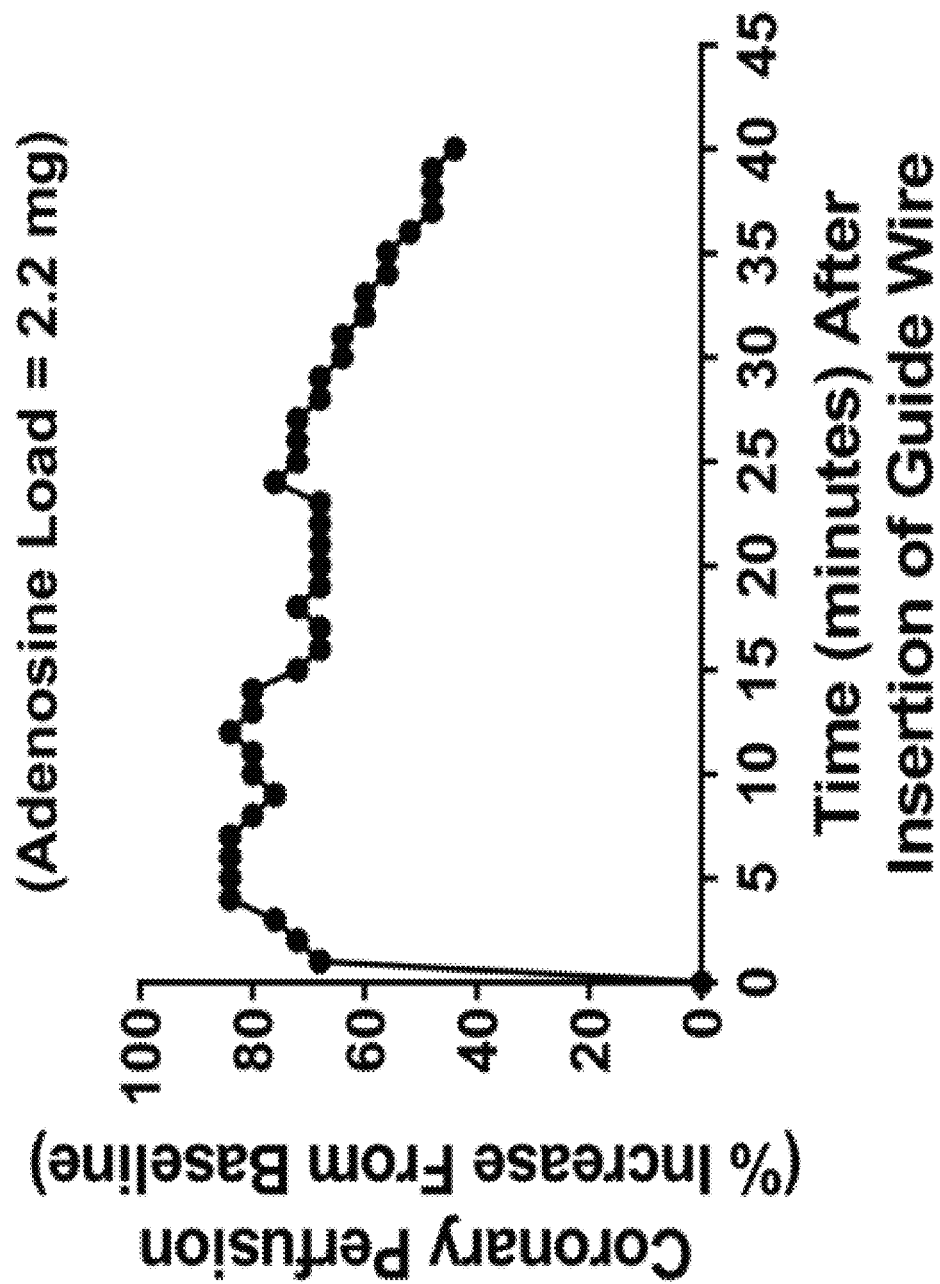
FIG. 8 shows a representative line graph illustrating the effects of an adenosine-releasing guidewire on coronary perfusion, as assessed by coronary blood flow velocity, in the pig in vivo. Note the rapid and sustained increase in coronary perfusion for 40 minutes.
Figure 9:
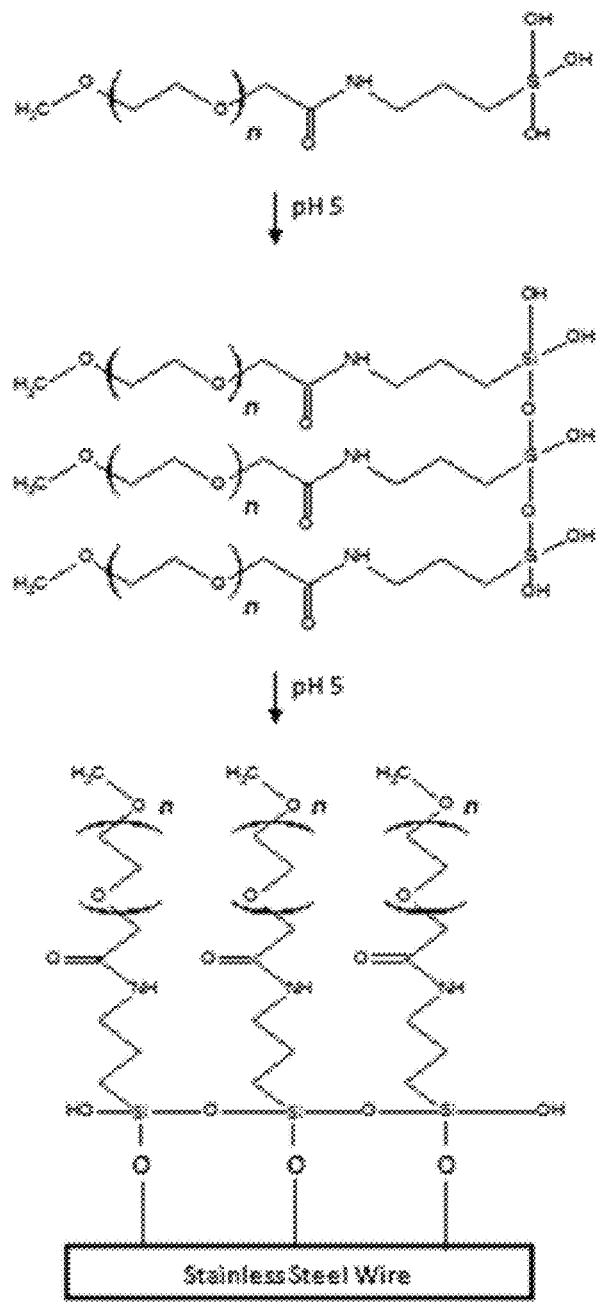
FIG. 9 illustrates a representative proposed mechanism of grafting PVA/PVP hydrogel to a stainless steel guidewire utilizing methoxy-PEG (m-PEG; aka triethoxy silyl ether PEG) as an intermediary coupling agent. Since m-PEG with high MW exhibits poor adhesion due to poor contact of the hydroxyl (OH) groups, surface modification is required. Guidewires were initially exposed to plasma treatment to create OH groups on the surface (Reaction 1). m-PEG was then hydrolyzed and acidified to produce a silanol with exposed OH groups (Reaction 2). This allows the m-PEG via condensation of the OH groups of the silanols to form a polymerized layer with the OH groups on the wire (Reaction 3). Grafting of the PVA/PVP hydrogel is then achieved via hydrogen bonding interactions between the carbonyl group of PEG and the hydroxyl group of PVA (Reaction 4).
Figure 9:
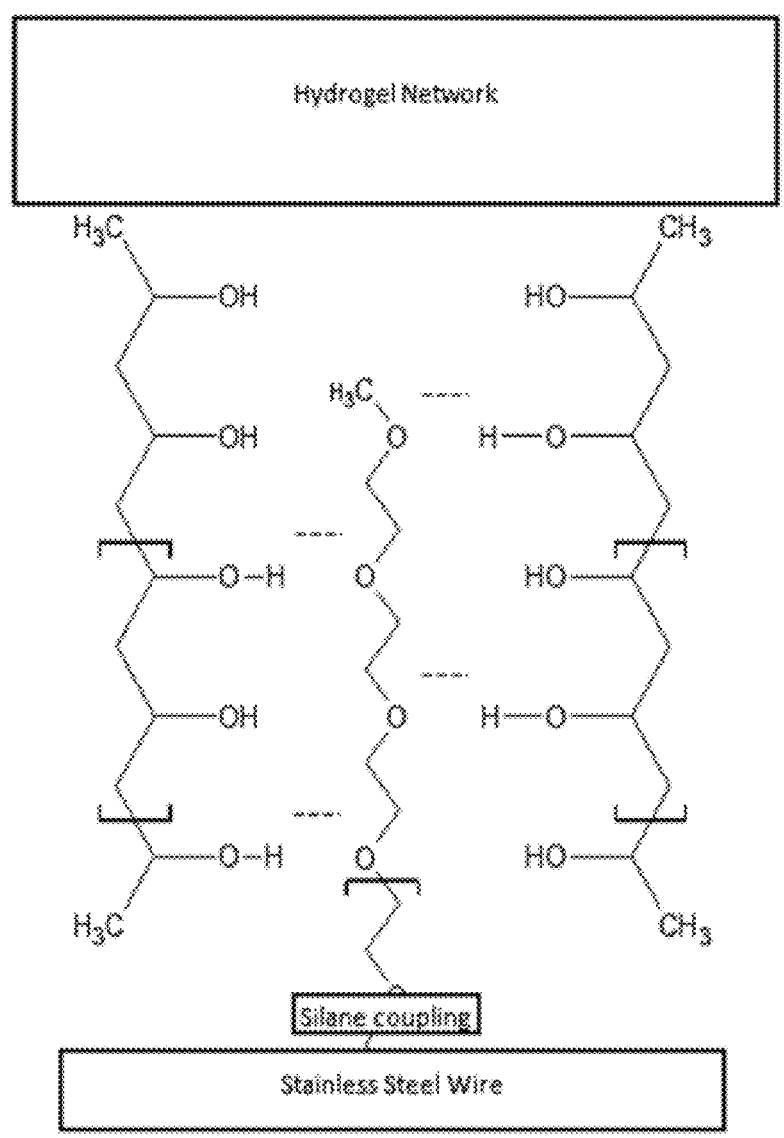

Without wishing to be bound by theory, the purpose of the experiment was to determine whether a PVA/PVP polymer containing the therapeutic agent adenosine as described in Example 1 would elicit a pharmacological effect by increasing coronary perfusion in the porcine model in vivo and whether the vasodilatory effect persisted for the duration of a typical PCI procedure of 30-40 minutes. Yucatan mini-pigs (25-30 Kg) were pre-medicated with Telazol (5 mg/Kg). Anesthesia was maintained with 1% isoflurane and supplemental oxygen to maintain a pH at 7.4+0.06. Animals received aspirin 300 mg orally for three days prior to the study and were anticoagulated throughout the procedure with heparin (150 units/Kg) to maintain ACT>300. Heart rate, EKG changes and blood pressure were monitored continuously with EKG leads and with a 6 F sheath in the femoral artery. Another sheath was inserted in the other femoral artery for coronary intubation of the left or right coronary ostia utilizing a 6Fr HS guide catheter. Coronary perfusion was measured as coronary blood flow velocity (CBFV) utilizing a 0.014 inch Doppler guide (Combowire; Volcano Corporation, Rancho Cordova, CA, USA) and dedicated software. CBFV was measured as continuous pulsatile velocity (cm/sec) and mean values were used in calculations. The Doppler wire was positioned in the mid portion of the circumflex vessel and baseline CBFV obtained. Care was taken to ensure the wire remained in the same position throughout the experiment. After baseline CBFV was measured, a guidewire (FIG. 1) coated with a PVA/PVP polymer and adenosine was positioned in the distal portion of the epicardial vessel and CBFV was measured serially every minute for 40 minutes. The drug-coated wire was then removed and CBFV measured until it had returned to baseline (2-3 minutes). As shown in FIG. 8 insertion of the polymer/drug guidewire resulted in an immediate increase in coronary perfusion of 1.5 to 2-fold which was maintained for 40 minutes. No change in heart rate or blood pressure were noted and no animal developed heart block. Coronary angiograms showed TIMI 3 flow following removal of the wire.

g. Example 6

It was determined that the use of traditional guidewire designs, due to limited surface area, could not provide an optimal drug load (Forman M B, Zhang J, Wu S, Mi Z, Hou D, Jackson E K. Development of a novel adenosine-eluting guidewire (Adenowire) for coronary vasodilation during percutaneous coronary intervention. Eurointervention 2014; 9: 23-32). Conventional wire designs were modified by increasing the coil spacing in the distal 15 cm of the wire to 0.005 inches while maintaining the wire performance and characteristics of the predicated device. Detailed drawings of the two wires are showed in FIG. 1. The wires are made of stainless steel and contain a coil spacing zone of 150 mm with slight variation in the placement of the radiopaque tungsten-platinum marker. The coil-wound section was left uncoated with the solid mandrel covered with proprietary teflon. Mechanical testing requirements of both wires (tensile testing of all joints, torque strength, torquebility, tip flexion and biocompatibility) met all the acceptance criteria and were similar to the predicate device.

Figure 11:
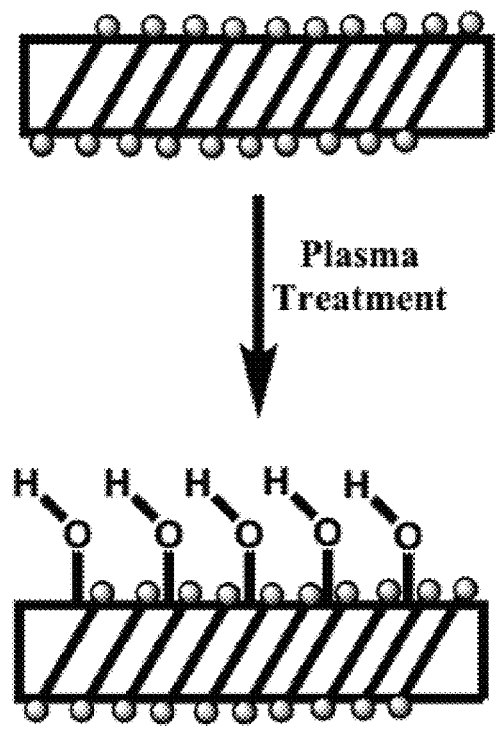
FIG. 11 illustrates chemical reactions in which guidewires were initially exposed to plasma treatment to create OH groups on the stainless steel surface of the guidewire.

The chemical reactions involved in coating the wire are illustrated in FIG. 11. The materials utilized for coating were PVA (MOWIOL 28-99, MW 145 kDa, EMO Millipore, US), PVAc (KOLLICOAT SR 30D, Sigma Aldrich, US), PVP (Providone K-30, Spectrum Chemical, US), methoxy-PEG-silane (Jenkem, Japan), and adenosine (Sigma Aldrich, US). Coronary guidewires as described above were cleaned in the distal 20-30 cm coiled region with an ultrasonic probe for five minutes in ethanol followed by deionized (DI) water for 5 min and dried via a nitrogen gas line (Ghosh A K, Bertels E, Allaer K et al. Effect of silane coupling agent on interfacial strength of stainless steel. 16th Eur. Conference Compos. Mater 2014; June: 1-5; Zhang F, Kang E T, Neoh K G, Tan, K L. Surface modification of stainless steel by grafting of poly(ethylene glycol) for reduction in protein absorption. Biomaterials 2001; 12: 1541-48; Holloway J L, Lowman A M, Vanlandingham M R, Palmese G R. Interfacial optimization of fiber-reinforced hydrogel composites for soft fibrous tissue applications. Acta Biomater 2014; 10: 3581-89).

Figure 12:
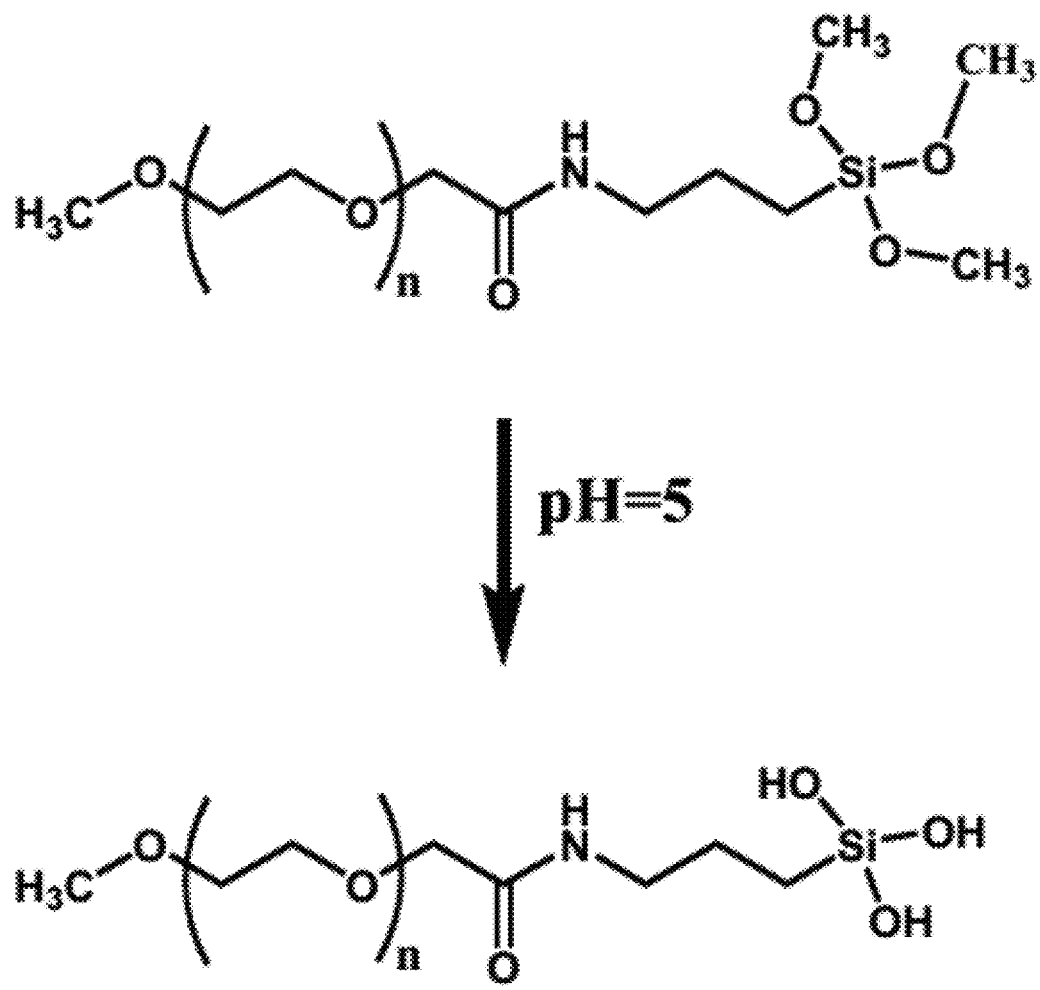
FIG. 12 illustrates the reaction in which methoxy-PEG-silane was treated with acid to hydrolyze the ester linkages, thus producing PEG-silanols with exposed OH groups.
Figure 13:
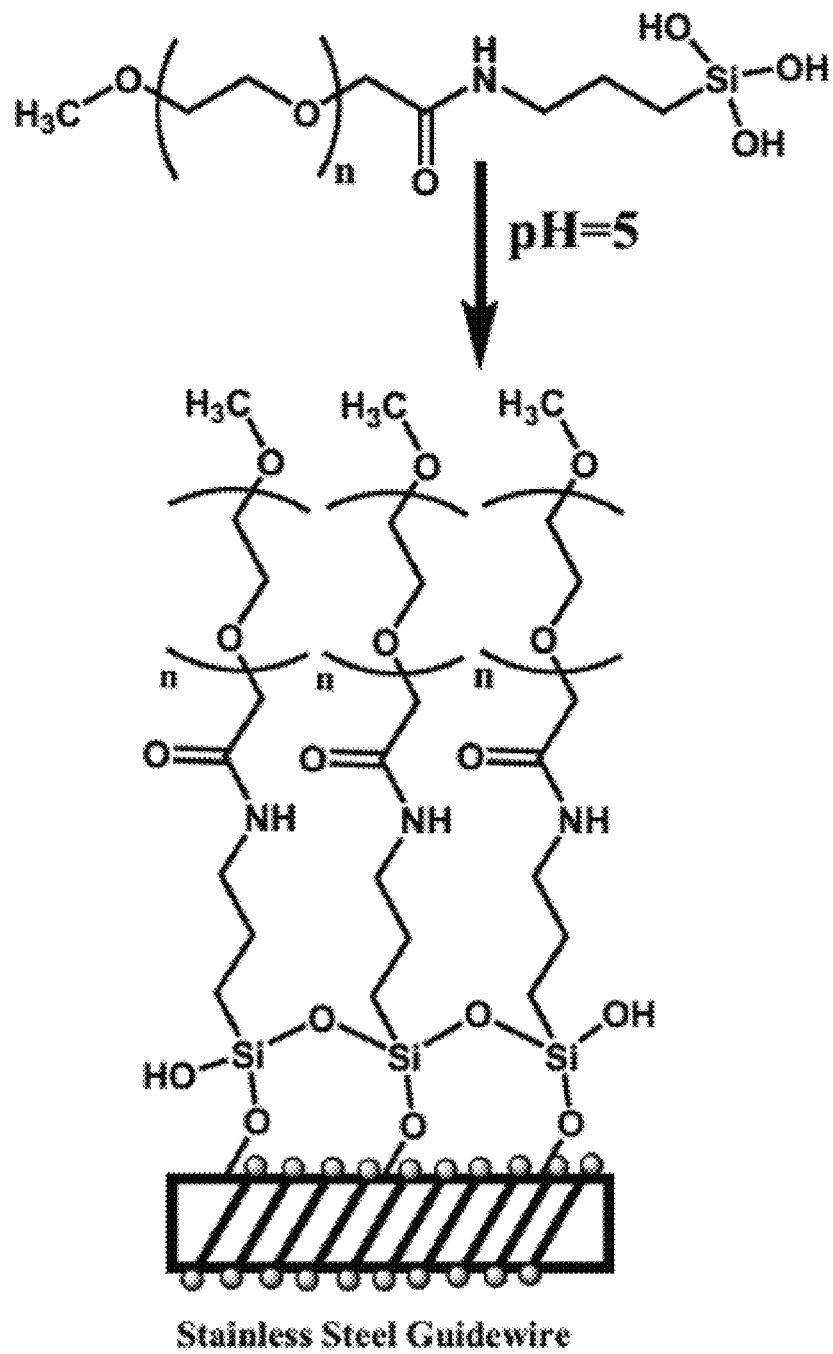
FIG. 13 illustrates the reaction in which PEG-silanols condensed with OH groups both on the wire and on neighboring silanols form a polymerized primer layer.

The wires were then subjected to oxygen plasma treatment for two minutes utilizing a commercial device (PE25-JW, Plasma Etch, Carson City, NV) which resulted in deposition of hydroxyl groups on the surface (FIG. 11, Reaction 1). A primer layer was then deposited on the wire utilizing methoxy-PEG-silane (MW, 20 kDa). A solution of methoxy-PEG-silane was prepared (40 mg/ml) in an ethanol/water solution (95/5 w/w) and titrated to a pH of 5.0 with glacial acetic acid. After 30 min to allow the methoxy-PEG-silane to hydrolyze (FIG. 12, Reaction 2), the wires were dipped in the hydrolyzed methoxy-PEG-silane mixture (now PEG-silanol solution) for 1 hr and cured at 70° C. for 90 min in a vacuum oven set at <0.1 bar. As shown in FIG. 13 (Reaction 3), the silanol groups covalently bond to the hydroxyl groups on the stainless steel and crosslink with neighboring silanol moieties to form a robust primer layer.

Figure 14:
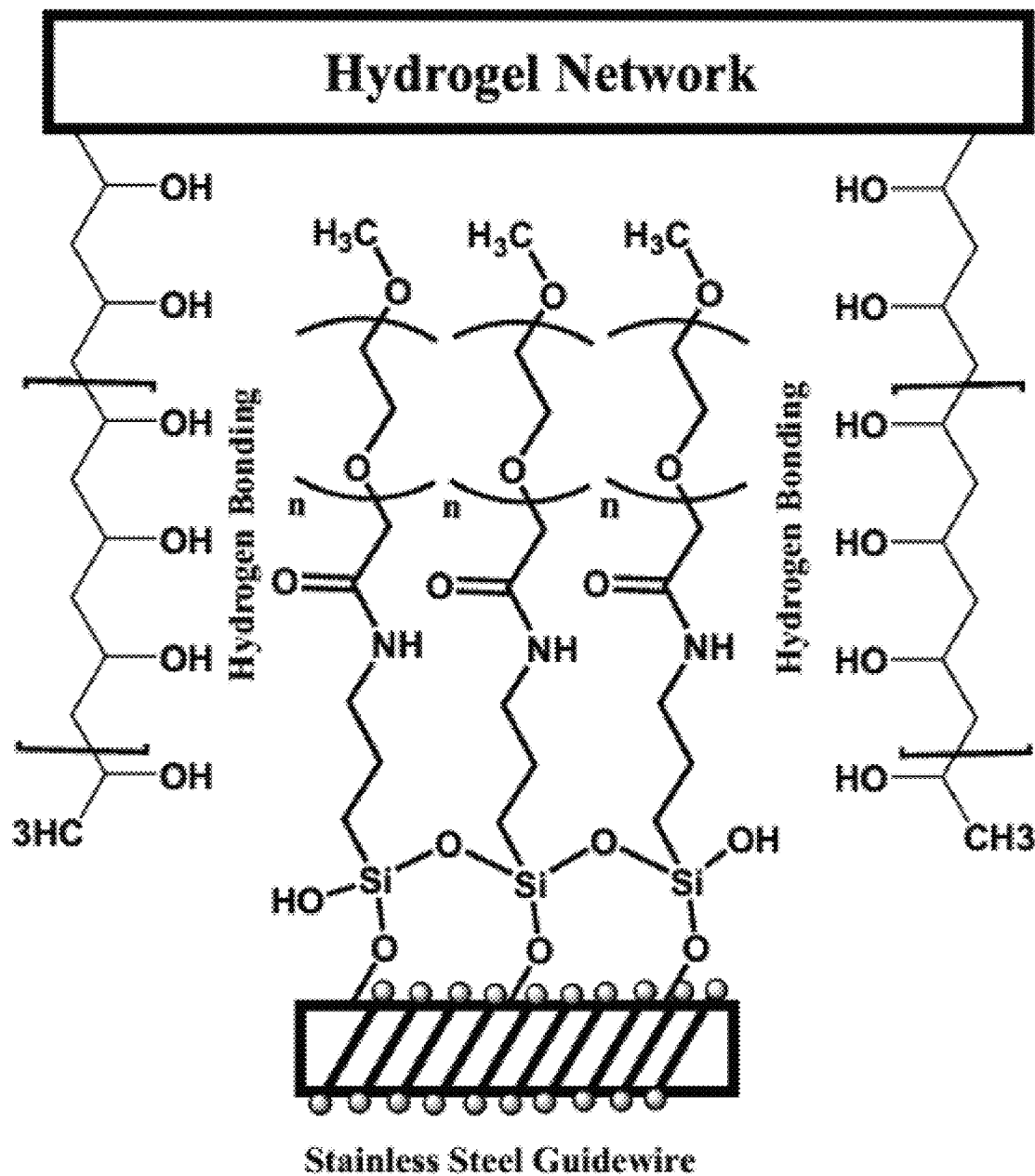
FIG. 14 illustrates the reaction to graft the PVA/PVP/PVAc hydrogel to the primer layer, which was achieved via hydrogen bonding interactions between the carbonyl, ether and amine groups of PEG and the OH groups of PVA.
Figure 15B:
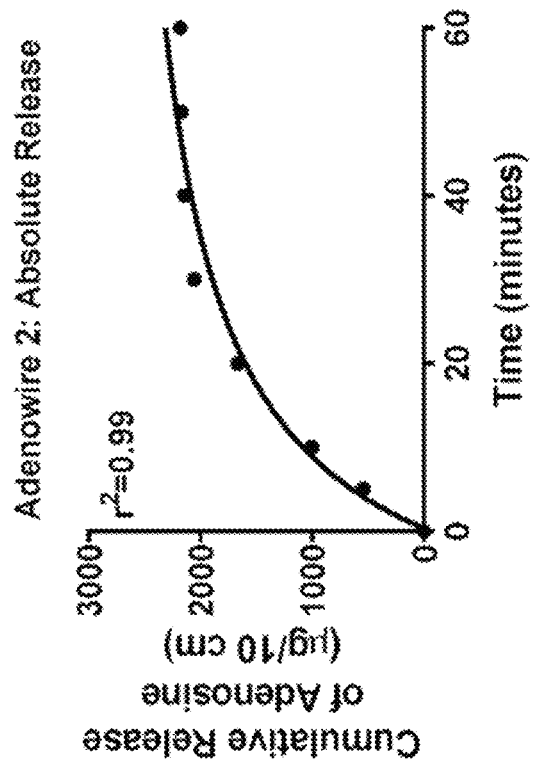
FIGS. 15A-F are line graphs demonstrating the elution profile of adenosine from six adenosine-loaded guidewires (Adenowires) in vitro. The release was curvilinear over approximately 60 min, a time frame which is suitable for an interventional procedure.
Figure 15A:
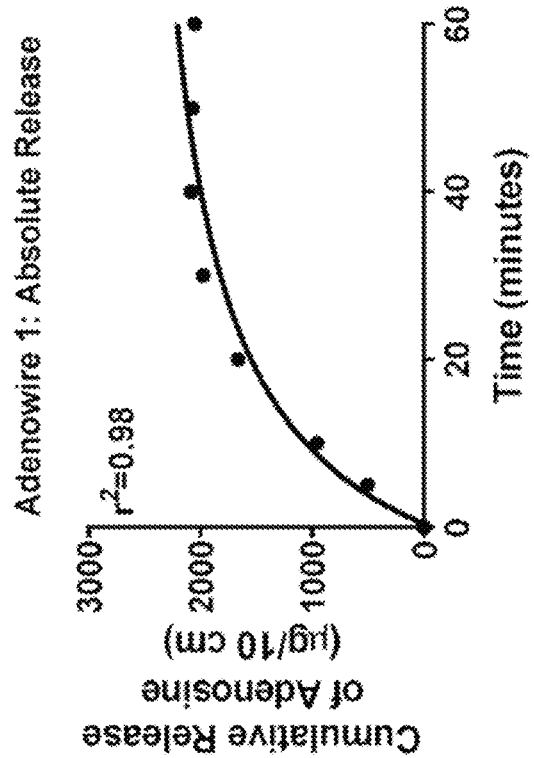
Figure 15D:
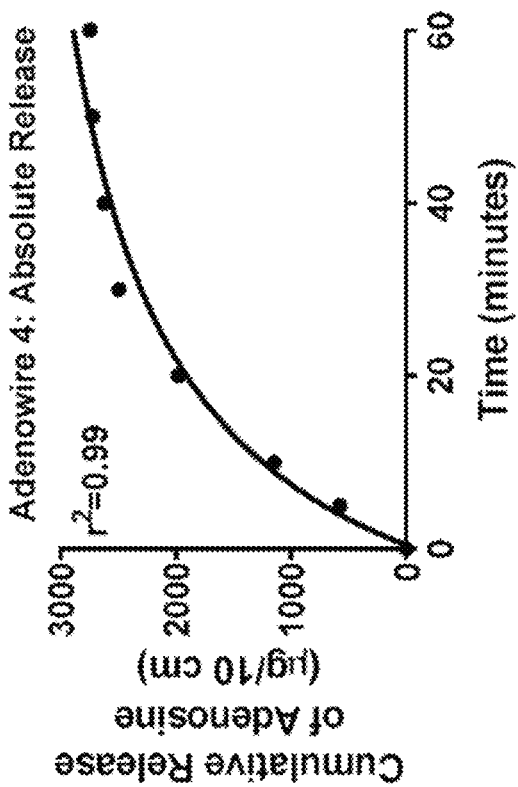
Figure 15C:
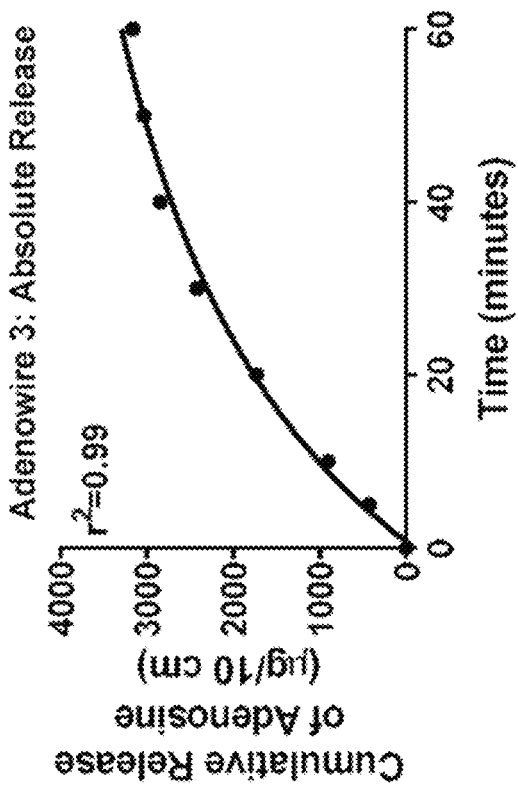
Figure 15F:
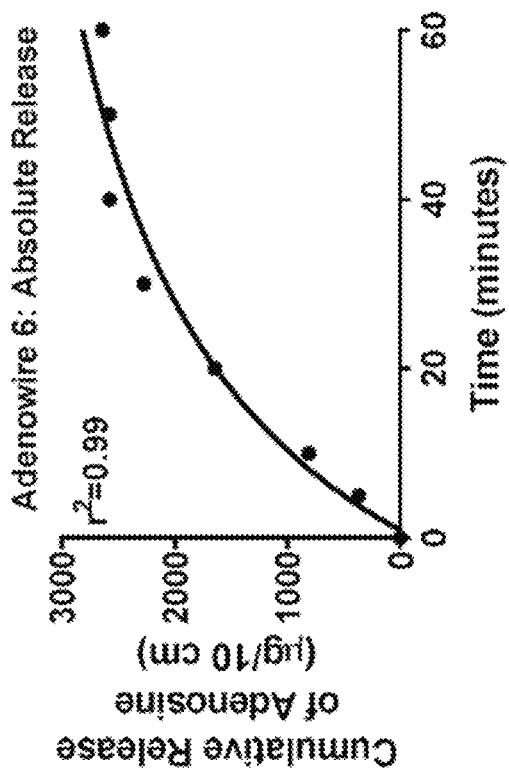
Figure 15E:
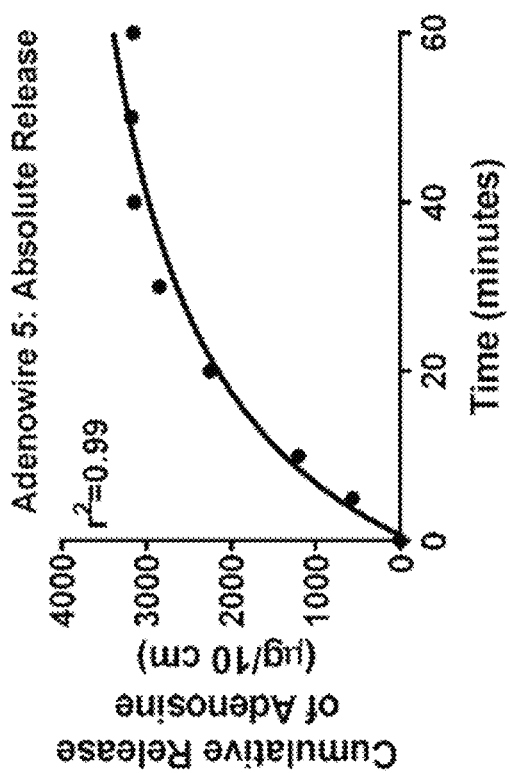

Next, the inner drug layer was prepared. In this regard, a 20% w/w solution of PVA/PVP (99:1 mass ratio) in DI water was prepared and autoclaved for 1 hr while stirring. This yielded a supersaturated solution which was homogeneous and free of bubbles. Using a water bath, the temperature of the PVA/PVP solution was maintained at 65° C. In order to create a sufficient drug load on the wire, a 25% concentration of adenosine was used in the drug layer. Adenosine has poor solubility in water (80 mg/mL) and commercial adenosine has a mean particle size of 55 microns which would have compromised the lubricity of the wire. Utilizing a two-pass jet-milling process, the solid phase adenosine particles were reduced in size to less than 5 microns. Micronized adenosine was mixed in DI water, sonicated for 15 min and then added to the PVA/PVP mixture and the PVA/PVP/adenosine mixture was stirred until a homogeneous solution was obtained. This resulted in a solution that contained 7.5% PVA, 67.5% water and 25% adenosine which was kept at 65° C. for the duration of the coating process. Next, the guidewire coated with the PEG-silanol primer was coated with the adenosine-containing hydrogel. Multiple hydroxyl groups in the hydrogel form hydrogen bonds with multiple ether oxygens in the primer, thus creating an extensive network of hydrogen bonds between the drug-containing hydrogel layer and the primer layer (FIG. 14, Reaction 4). This results in a stable attachment of the drug layer with the wire surface. Laser diffraction and optical microscopy demonstrated stable particle sizes of the jet-milled adenosine even after one week in the hydrogel.

The barrier (outer) layer was produced using PVA with PVAc in a ratio of 1:3 (w/w). A 20% solution of PVA without PVP was prepared as described above. Commercially available PVAc packaged as a 30% dispersion with stablilizer and excipients was added to the PVA solution and mechanically mixed at 65° C. to achieve a homogeneous solution. The final solution, consisting of 5% PVA, 80% DI water and 15% PVAc, was left at room temperature.

The wires were coated utilizing a mechanical dipper (Precision Dip Coater QPI-168, Qualtech, Denver, CO) with insertion and withdrawal parameters set to obtain a total polymer weight of approximately 45 mg per 10 cm length of wire. For the drug layer an insertion rate of 200 mm/min, dwell time of 10 secs and withdrawal rate of 40 mm/min was employed. After applying the drug layer, the wire was immediately flash frozen in liquid nitrogen and subjected to a 60 min freeze/thaw cycle: 45 min at −20° C., followed by a thawing at room temperature. This freeze/thaw cycle was then repeated to harden the gel. The wire was then coated with the barrier layer utilizing a withdrawal rate of 500 mm/sec, after which the wire was subjected to a further two freeze/thaw cycles. The final product contained a total polymer weight per 10 cm length of wire of approximately 40 to 45 mg with a drug load of 2.7±0.2 mg of adenosine per 10 cm length of wire.

In vitro release studies were performed in 0.9% saline rather than in plasma or blood because adenosine has a short half-life (seconds) in the latter two media making detection difficult. Tubes containing 15 ml saline were maintained at 37° C. and 10 cm of the spaced coiled section of the guidewire was placed serially in tubes for 0 to 5, 5 to 10, 10 to 20, 20 to 30, 30 to 40, 40 to 50, and 50 to 60 minutes. One ml samples were then taken from the tube to measure the concentration of adenosine by spectrophotometry (Jackson E K, Mi Z, Koehler M T, Carcillo J A Jr, Herzer W A. Injured erythrocytes release adenosine deaminase into the circulation. J Pharmacol Exp Ther 1996; 279: 1250-60).

Animal Studies: All porcine studies were approved by Institutional Animal Care and the Committee of Synchrony Labs LLC, NC. Yucatan mini pigs (25 to 30 Kg) were premedicated with Telazol (5 mg/Kg). Anesthesia was maintained with 1% isoflurane and supplemental oxygen to maintain a pH of 7.4±0.6. Animals received aspirin 300 mg orally for three days prior to the study and were anticoagulated throughout the procedure with heparin (150 units/kg) to maintain ACT greater than 300. Heart rate, EKG changes and blood pressure were monitored continuously utilizing leads I, AVF and AVL with a 6 F sheath in the left femoral artery. Another sheath was placed the right femoral artery for coronary intubation of the left main vessel utilizing a 6 F HS guide catheter. Coronary blood flow velocity (CFV) was measured utilizing a 0.014-inch Doppler flowwire (Combowire, Volcano Corporation, Rancho Cordova, CA, USA) and dedicated software. CFV was measured as a continuous average pulse wave velocity over 4 seconds and mean values were recorded every 60 seconds.

Two experimental protocols were employed. In the first protocol, the efficacy and duration of vasodilatation induced by the wire under basal conditions were assessed. The Combowire was positioned in either the proximal circumflex (LCX) or left anterior descending (LAD) coronary artery and baseline CFV was measured after obtaining an optimal velocity tracing. Care was taken to ensure that the Doppler wire remained in the same position throughout the experiment. An adenosine-containing guidewire was positioned in the distal LCX or LAD, and heart rate, blood pressure and CFV was measured serially every min for 30 min. The drug-coated wire was removed and CFV was measured until it had returned to baseline. Serial coronary angiography was performed at baseline, after Combowire placement and after removal of the medicated guidewire.

In the second protocol the ability of the wire to prevent and reverse intense vasoconstriction induced by intracoronary administration of acetylcholine (Ach) was evaluated. Release of numerous potent vasoconstrictors plays a role in the pathogenesis of NRF. Ach is a powerful vasoconstrictor in the porcine model via direct muscarinic activation of smooth muscle cells in small coronary arteries resulting in NRF (Hata, H., et al., Cor. Art. Dis., 4:891 (1993). A Transit infusion catheter (Codman, Roynham, MA) was placed in the proximal LAD for the drug infusion. Ach doses of 0.3 to 1.0 mg/min were infused into the LAD for 20 to 30 min. Preliminary studies showed that this results in an approximate 80% reduction in CBFV. In some studies Ach was commenced initially and after a greater than 50% decrease in CBFV was observed, an adenosine-loaded guidewire was rapidly inserted into the distal vessel for 15 to 20 min. These studies were designed to determine if the wire could reverse the NRF. In other experiments, we evaluated whether an adenosine-releasing wire could prevent the NRF by placing the adenosine-loaded wire initially into the LAD. Once an increase in CFV had occurred an Ach infusion was begun for 20 to 30 min. In some studies, the wire was removed at 20 min and the Ach infusion continued, while in others the Ach infusion was terminated and the wire was left in place for a further 10 min in the vessel.

Since guidewires are utilized to place a device into coronary vessels, it is essential that guidewires easily negotiate a tortuous vasculature to facilitate placement of devices without inducing vascular damage. To assess guidewire lubricity, a two-dimensional coronary model system (ASTM 2394) and a MSI IDTE 3000 device with dedicated software were utilized (Machine Solutions, Flagstaff, Az). A 6 F coronary guide catheter was introduced 3 cm into the mock vessel. The wire was inserted through a hemostatic valve into the catheter and tracked for 3 cycles in the model for a distance of 38 cm. A proximal load cell with an encoder was used to measure the force applied to deliver and retract the guidewire and the distance in and out of the model. Microscopic images were obtained at baseline, after the track test and after hydration for one hour. Wire performance was determined in vitro and in vivo and included the ability to navigate the model or vessel, torqueability and tip flexibility.

For statistical analyses, data are expressed as mean±SEM. Changes in heart rate, systolic, diastolic and mean blood pressure, CFV and coronary flow reserve (CFR) were assessed with analysis of variance for repeated measures followed by Bonferroni's multiple comparison test. Differences were considered significant when $P<0.05$.

Figure 16B:
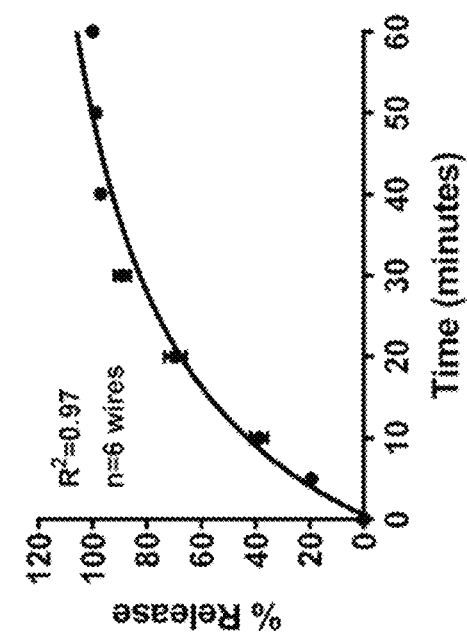
FIGS. 16A-B are line graphs depicting the average elution profile from the six adenosine-loaded guidewires shown in FIGS. 15A-F. The results are plotted either as cumulative release of absolute amounts of adenosine (left panel) or as % release relative to the 60-min timepoint (right panel). The average release at 60 min was 2.7±0.2 mg per 10 cm of length. Values are means±SEM.
Figure 16A:
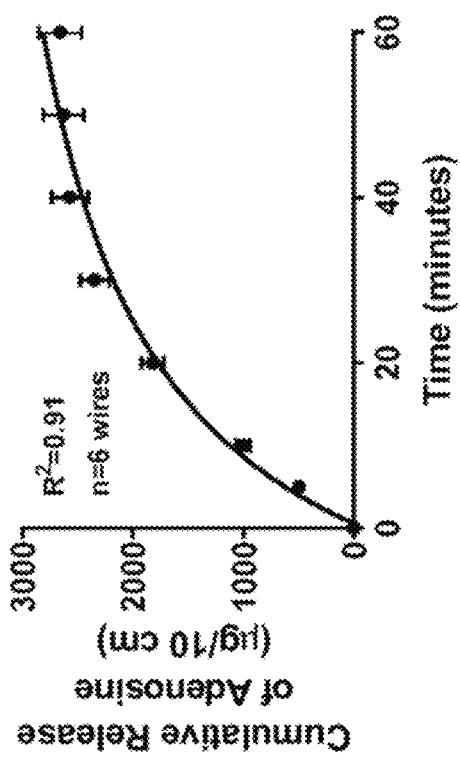

The cumulative elution of adenosine from six guidewires over 60 min is illustrated for each individual guidewire in FIGS. 15A-F. FIGS. 16A-B depict the cumulative average release from the composite of all 6 guidewires, with results expressed as either absolute release (left panel) or release relative (% of 60-min timepoint; right panel). As shown, the release of adenosine was curvilinear with approximately 60% released in the first 20 min and most of the remainder by 40 min. This release profile is optimal for a typical coronary interventional procedure with the initial burst treating and the sustained release preventing NRF. The total amount of released adenosine was 2.7±0.2 mg/10 cm length of wire.

Figure 17B:
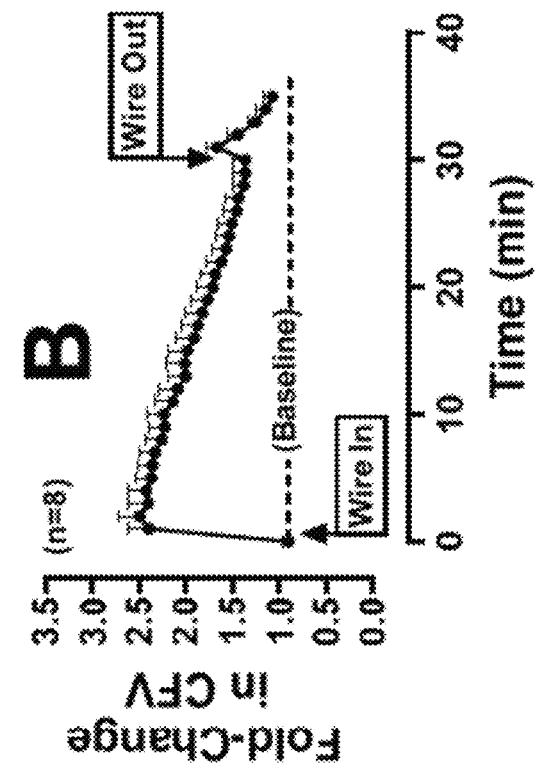
FIGS. 17A-D are line graphs summarizing the effect on coronary flow velocity (CFV) of adenosine-releasing guidewires (n=8) inserted into the LAD or LCX in Yucatan mini-pigs. Coronary flow velocity (FIG. 17A) was markedly increased immediately upon wire insertion and remained significantly elevated for 27 min.
Figure 17A:
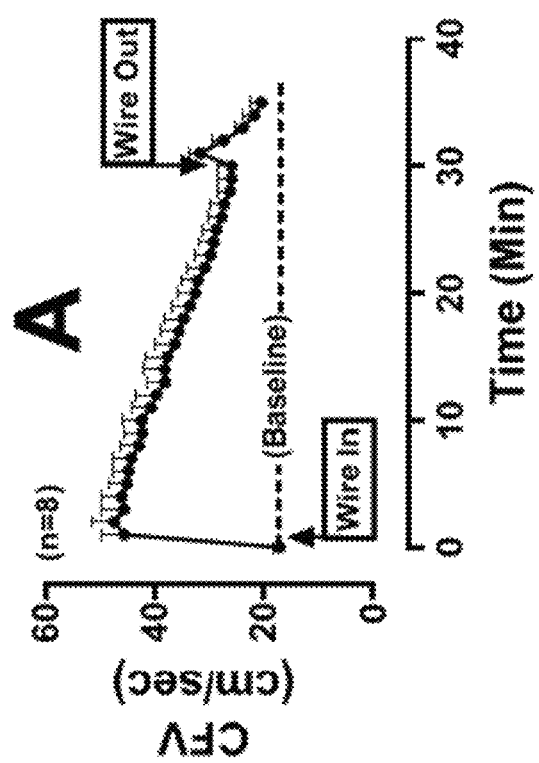
Figure 17C:
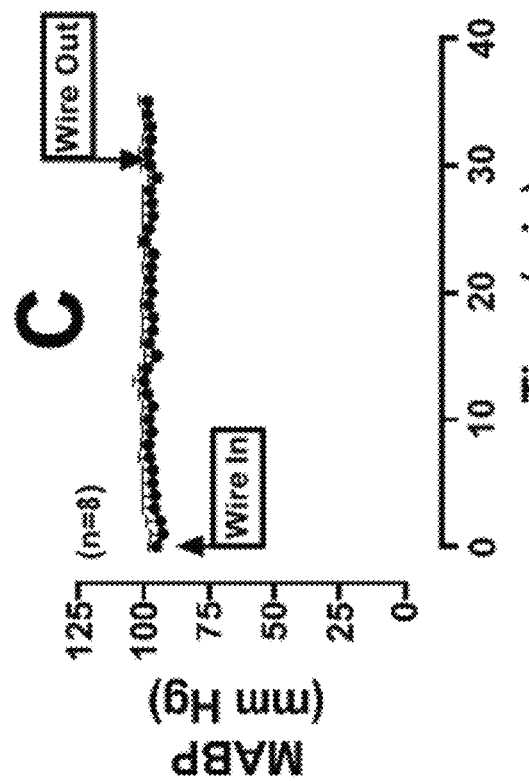
Figure 17D:
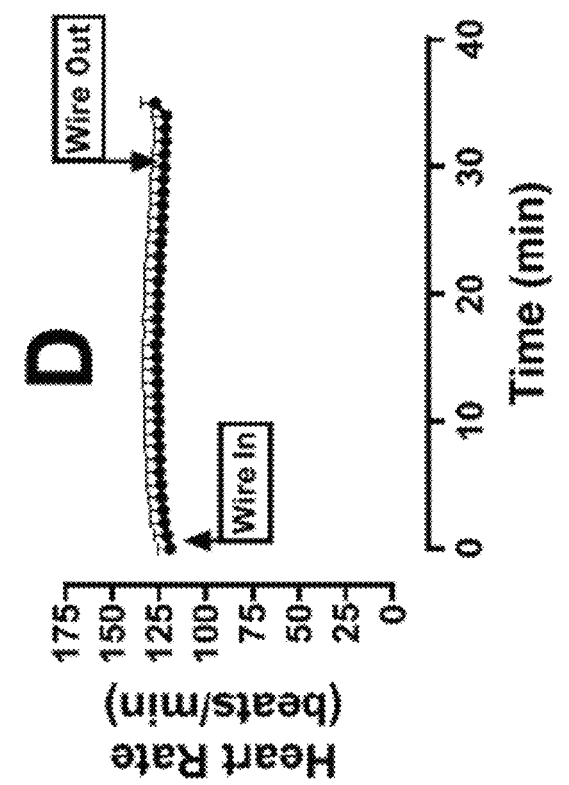
Figure 19B:
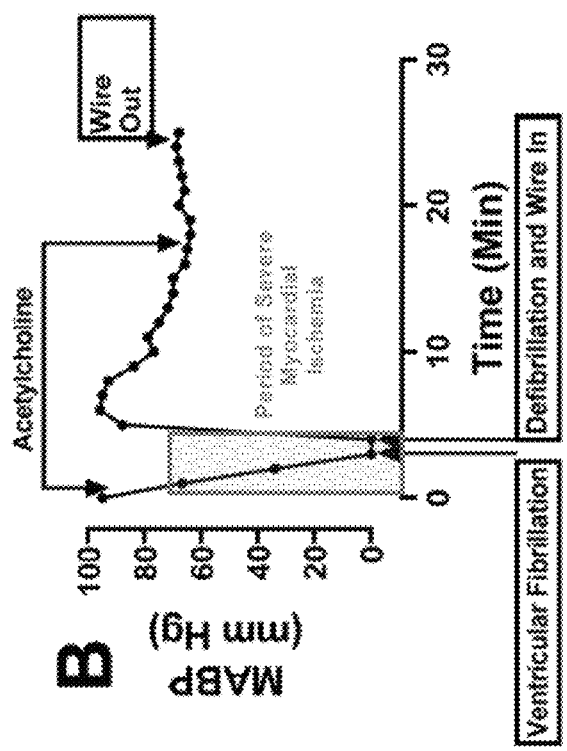
FIGS. 19A-F are line graphs summarizing three experiments in which acetylcholine was infused into the coronary artery before the adenosine-loaded guidewire was inserted into the artery. Experiment one is summarized in FIGS. 19A-B; experiment two in FIGS. 19C-D; and experiment three in FIGS. 19E-F. Coronary flow velocities (CFV) are illustrated in FIGS. 19A, 19C and 19E and associated mean arterial blood pressures (MABP) are shown in FIGS. 19B, 19D, and 19F. In experiment one, the animal developed severe ischemia that induced ventricular fibrillation requiring cardioversion. In all three experiments, acetylcholine causes coronary vasoconstriction that was reversed by insertion of the adenosine-releasing guidewire.
Figure 19A:
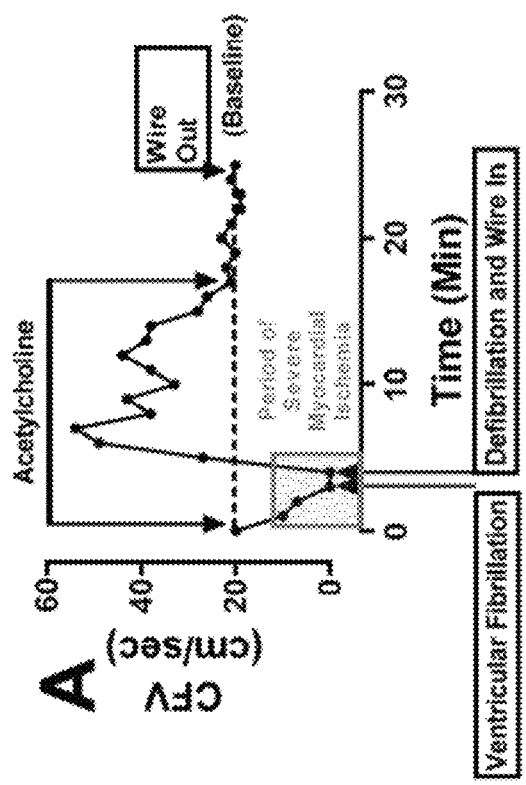
Figure 19D:
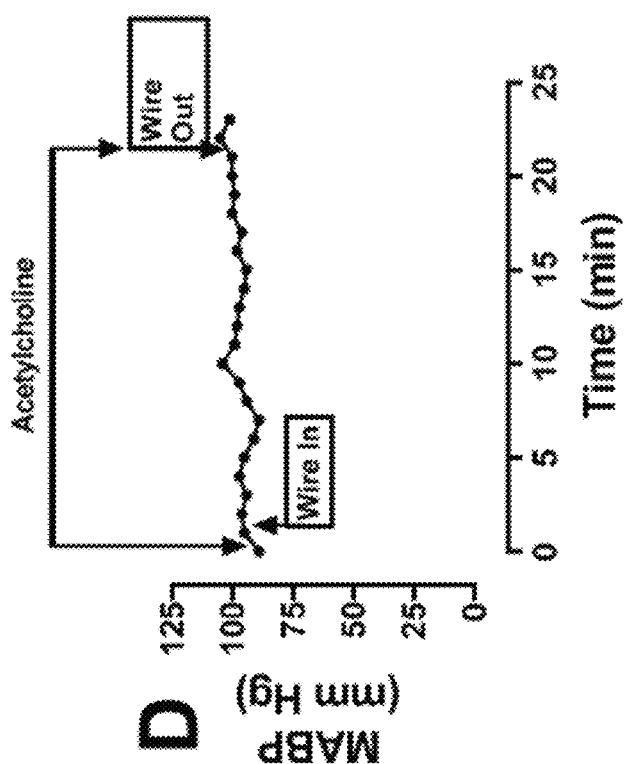
Figure 19C:
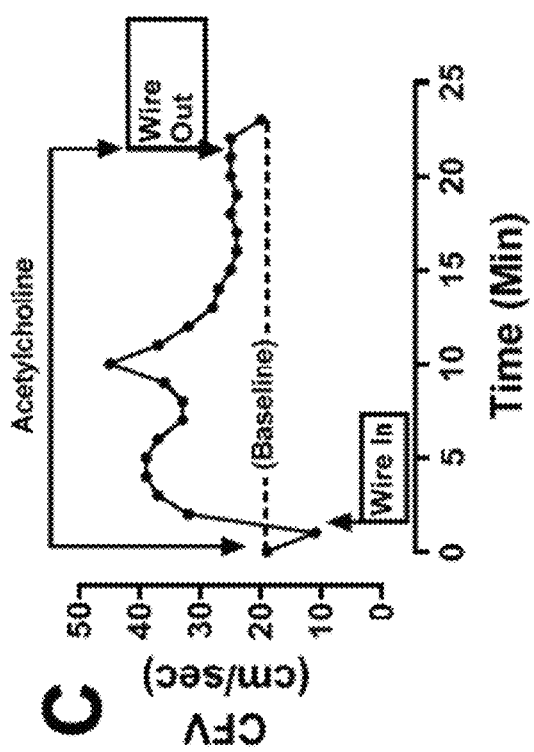
Figure 19F:
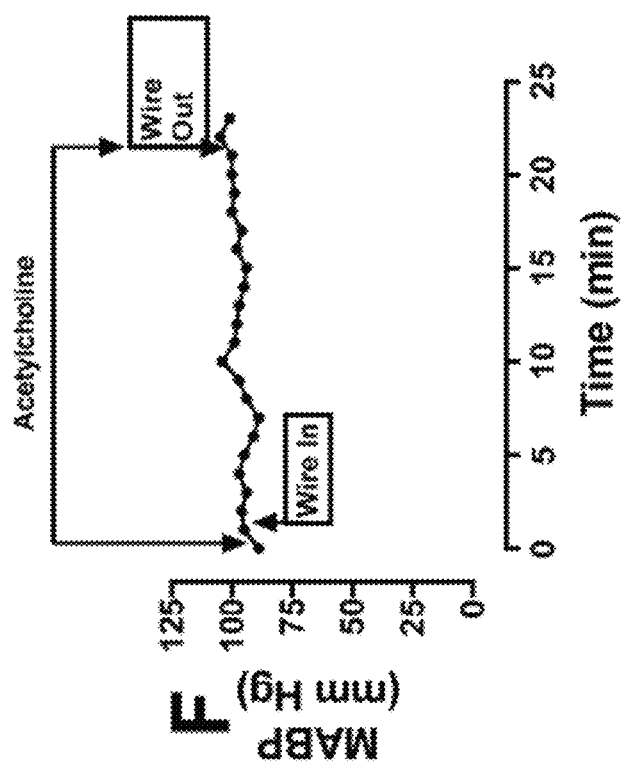
Figure 19E:
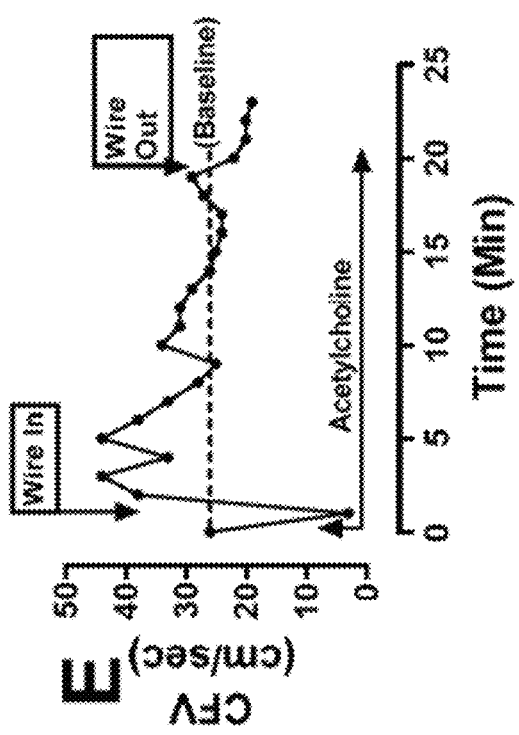
Figure 20D:
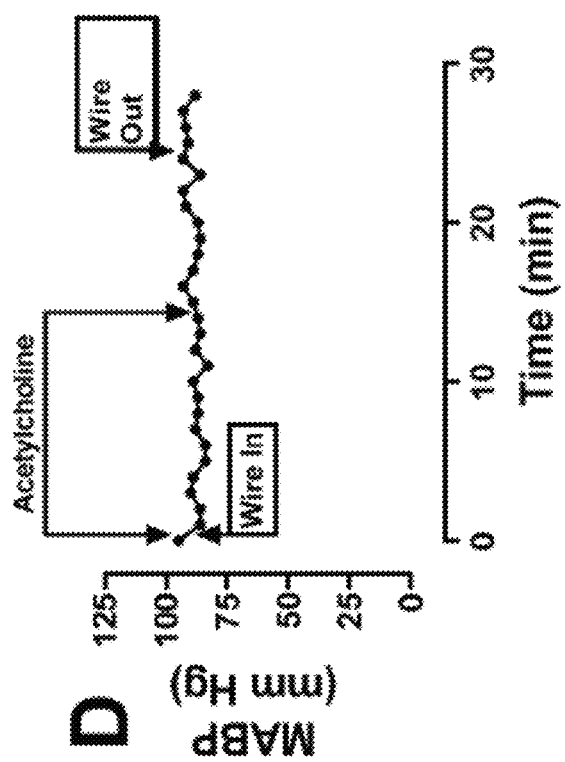
Figure 20C:
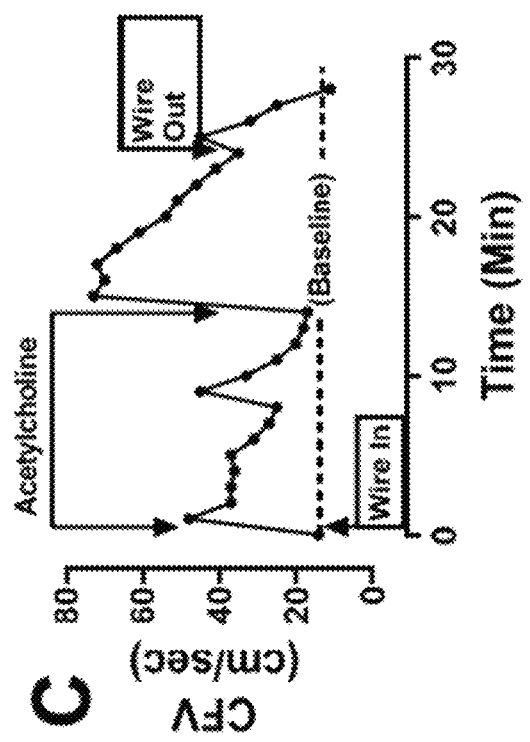
Figure 20F:
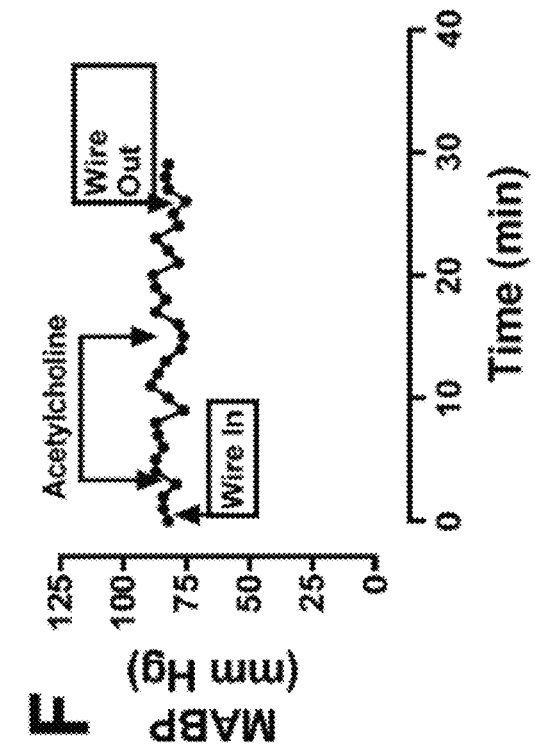
Figure 20E:
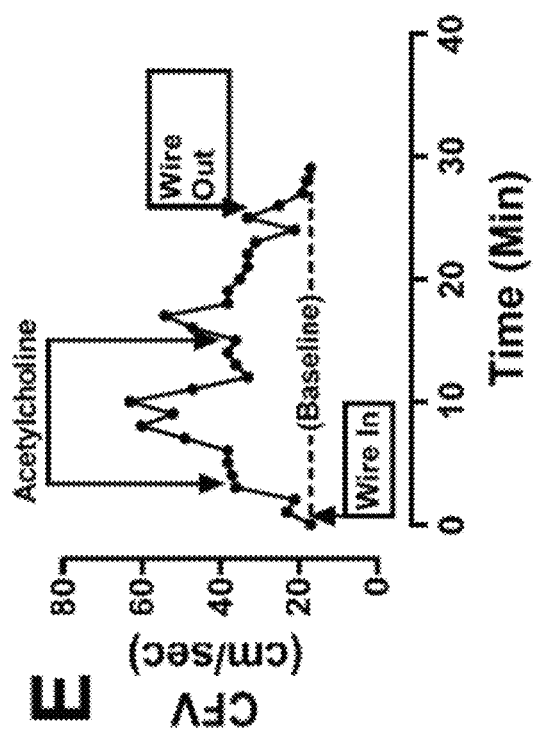

Effect of Adenosine-Releasing Guidewire on Basal Coronary Flow in the Pig: The effect of eight guidewires on CFV in the LCX and LAD is shown in FIG. 17A. CFV increased within one min of guidewire insertion and remained significantly elevated above baseline for 27 minutes. This increase in CFV closely paralleled the adenosine-release profile in vitro. The fold increase in CFV (FIG. 17B), a measure of CFR, peaked at 2.5 and remained greater than 2.0 for 15 min after wire insertion. Previous studies showed that a continuous infusion of adenosine into the LAD at 50 µg/kg/min increased CFV approximately 250%. Insertion of adenosine-releasing guidewires did not affect either mean arterial blood pressure (FIG. 17C) or heart rate (FIG. 18D), and no animal developed heart block. Coronary angiography after each guidewire removal showed normal flow and no filling defects (FIGS. 18A-C).

Effect of Adenosine-Releasing Guidewire on Ach-Induced Coronary Vasoconstriction in the Pig: FIGS. 19A-F summarize the results of three experiments in which acetylcholine was infused into the coronary artery to induce coronary vasoconstriction, and then an adenosine-releasing guidewire was inserted. In the first experiment of this type (FIGS. 19A and 19B), coronary vasoconstriction was so intense that coronary flow ceased and the animal rapidly developed ventricular fibrillation. The heart was immediately defibrillated and an adenosine-releasing wire was inserted into the coronary artery. Despite continuing the acetylcholine, immediately upon insertion of the adenosine-releasing wire, CFV not only was restored but more than doubled from pre-acetylcholine baseline. CFV gradually returned to baseline and the acetylcholine infusion was stopped and then the guidewire was removed. In two similar experiments (FIGS. 19C, 19D, 19E and 19F), insertion of the adenosine-releasing guidewire immediately reversed acetylcholine-induced coronary vasoconstriction and maintained CFV either above or near baseline during the acetylcholine infusion.

Figure 21D:
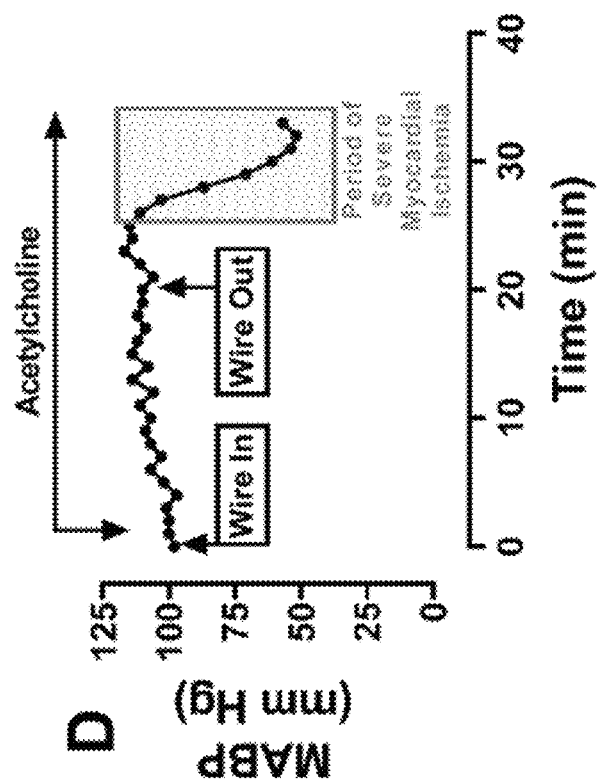
Figure 21C:
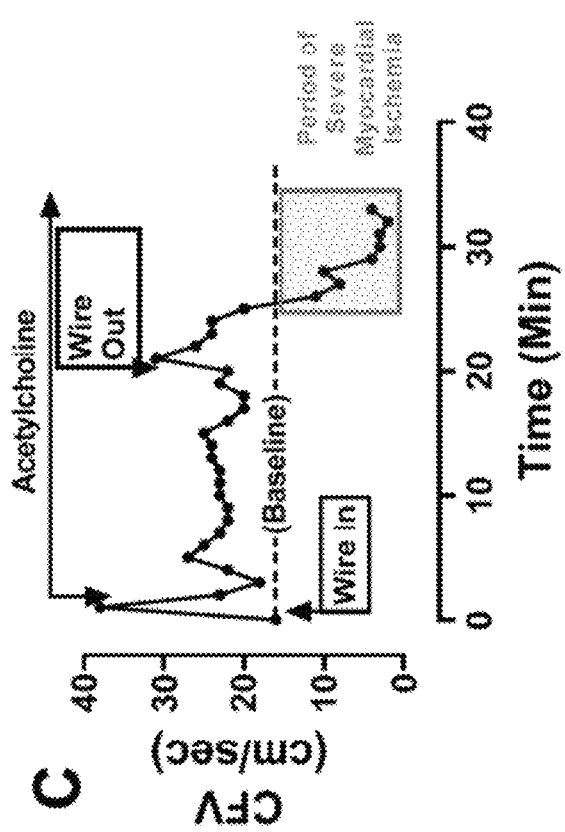

Together, FIGS. 20A-F and FIGS. 21A-D summarize the results of five experiments in which an adenosine-releasing guidewire was inserted before infusing acetylcholine into the coronary artery. As shown, in all experiments, insertion of the guidewire increased CFV and maintained CFV above baseline even when acetylcholine was infused. As shown in FIG. 21C, the adenosine-releasing guidewire elevated CFV above baseline even while acetylcholine was infused. While maintaining the acetylcholine infusion, the guidewire was removed, and CFV rapidly began to fall nearly to zero. Coronary angiography in two animals showed acute NRF with restoration of coronary patency after insertion of an adenosine-releasing guidewire (FIGS. 22A-D).

Figure 10A:
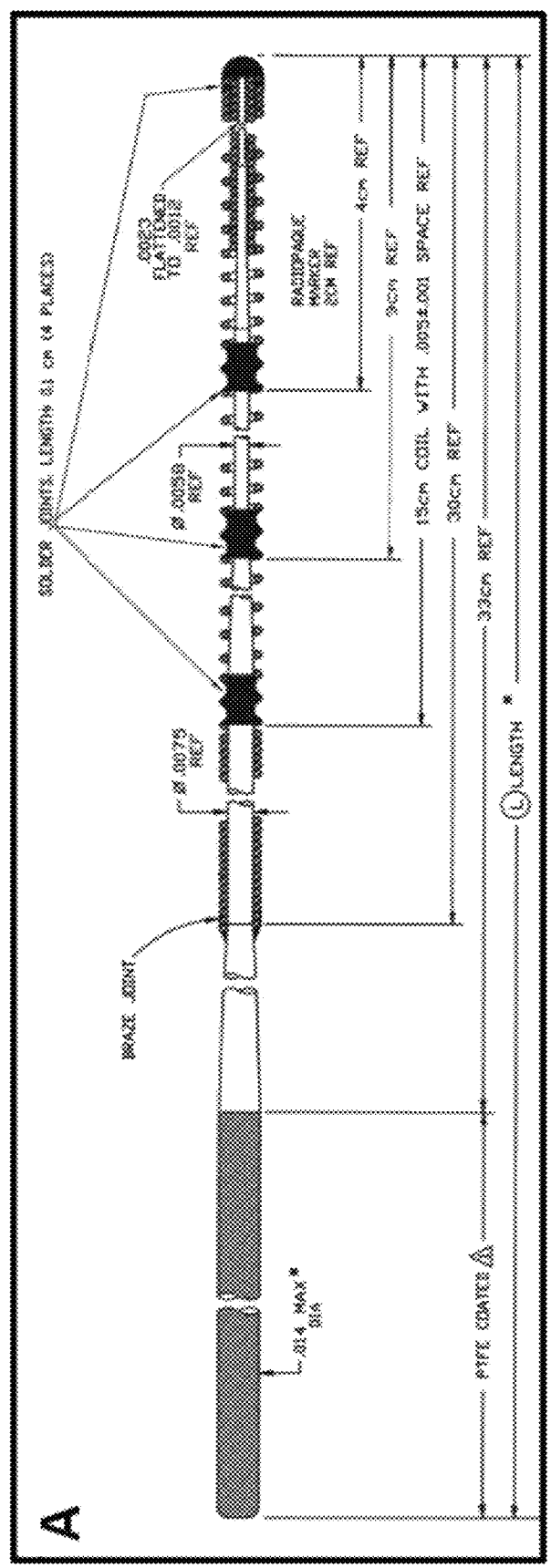
FIGS. 10A-D illustrate two types of 0.014-inch stainless steel guidewires utilized for this disclosure. Adenosine-releasing guidewires were redesigns of two commercially approved wires (0.014 inch stainless steel) which were modified by increasing the coil spacing to 0.005 inches in the distal 15 cm in order to accommodate the hydrophilic-drug polymer.
Figure 10B:
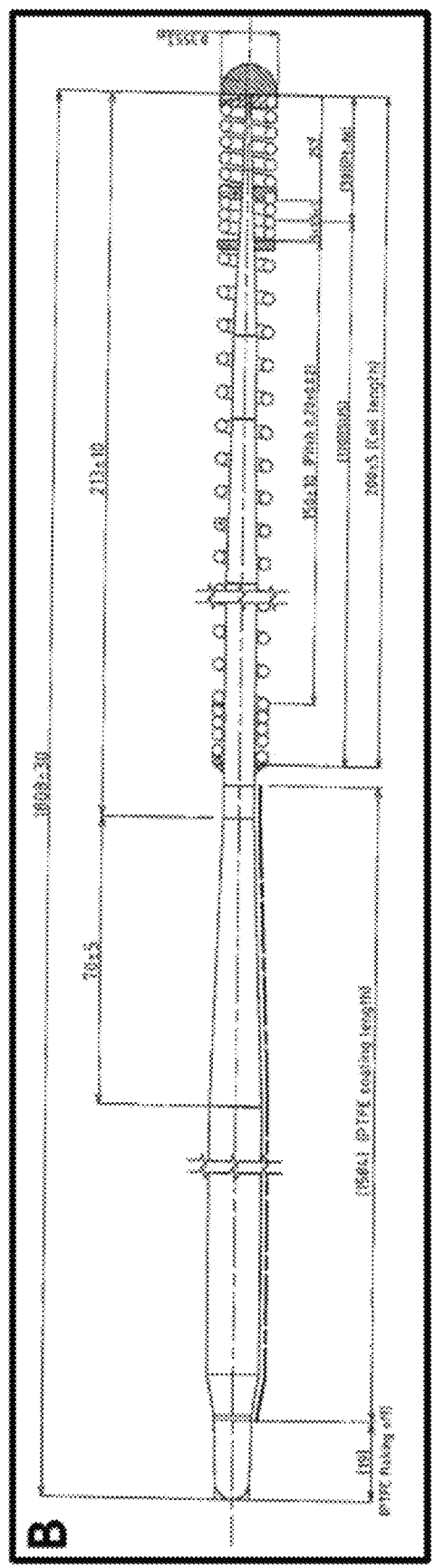
Figure 10D:
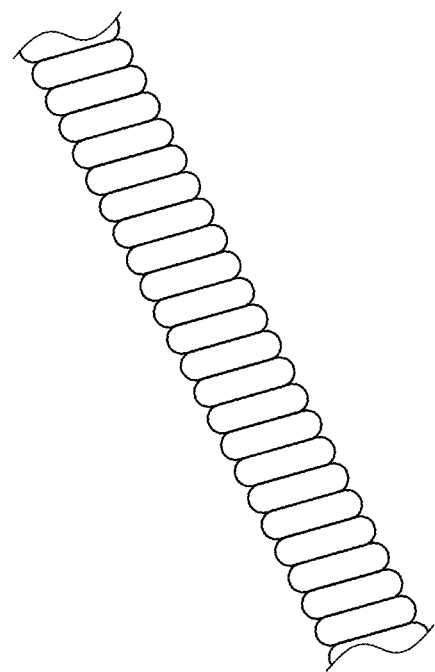
Figure 10C:
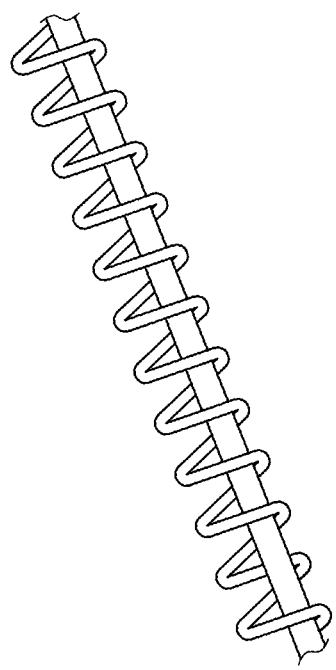
Figure 23:
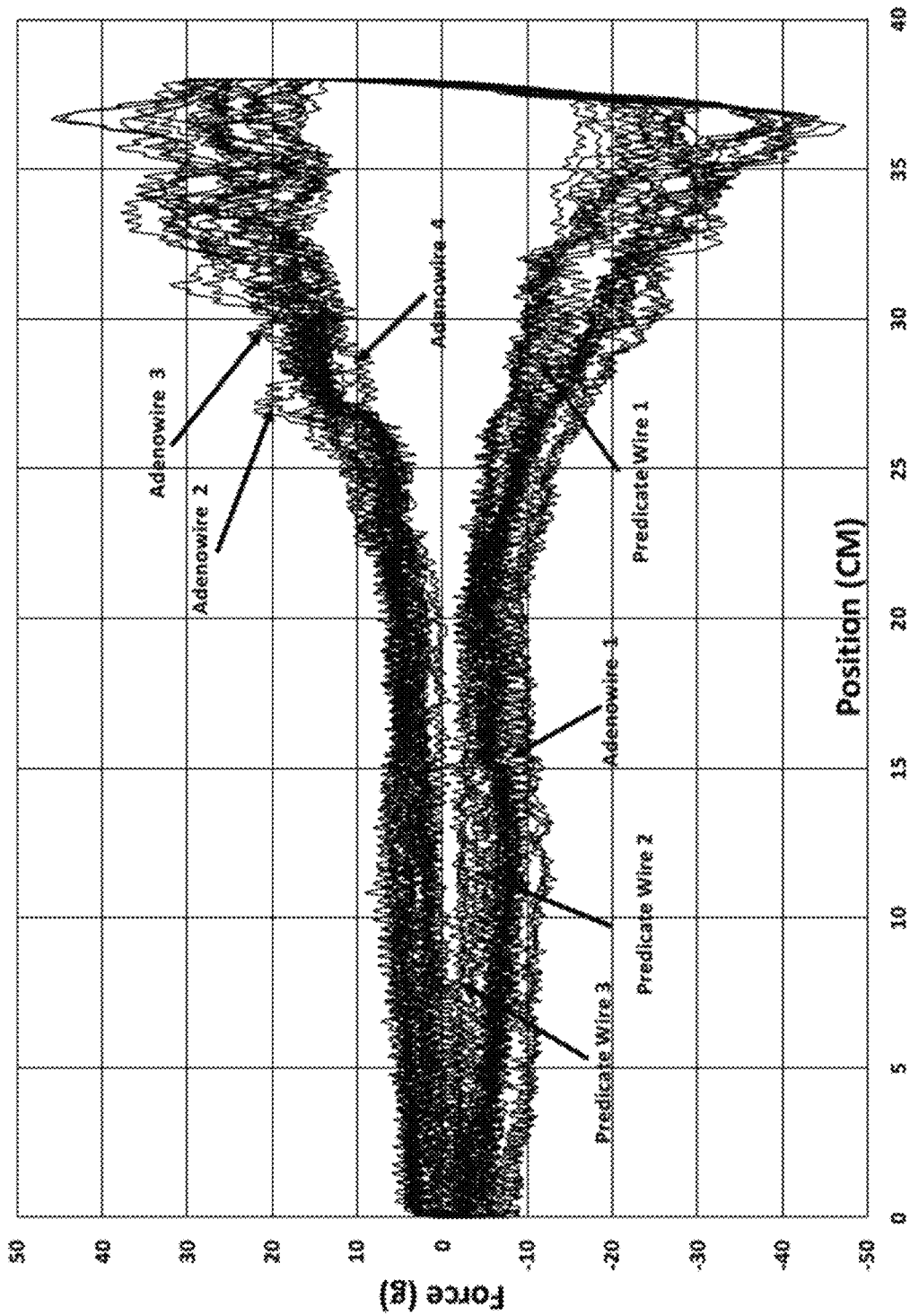
FIG. 23 is a plot of track forces (grams) of 4 Adenowires and 3 commercial wires with a hydrophilic coating. The insertion and withdrawal forces were similar indicative of comparable lubricity properties.

Evaluation of Guidewire and Coating Performance. Light microscopy of unused wires (FIGS. 10C and 10D) demonstrated that the hydrogel-drug coating filled the coil spaces and provided a smooth and thin coating on the outer coil surface. Track forces were obtained on 4 Adenowires and 3 predicated hydrophilic wires (Prowater, Asahi-Intecc, Seto, Jp). The frictional forces to deliver and retract the Adenowires were similar to the commercial wires indicative of similar lubricity properties (FIG. 23). Light microscopy after track tests and hydration revealed that the coating integrity remained unchanged with no evidence of swelling or coating loss.

Figure 24D:
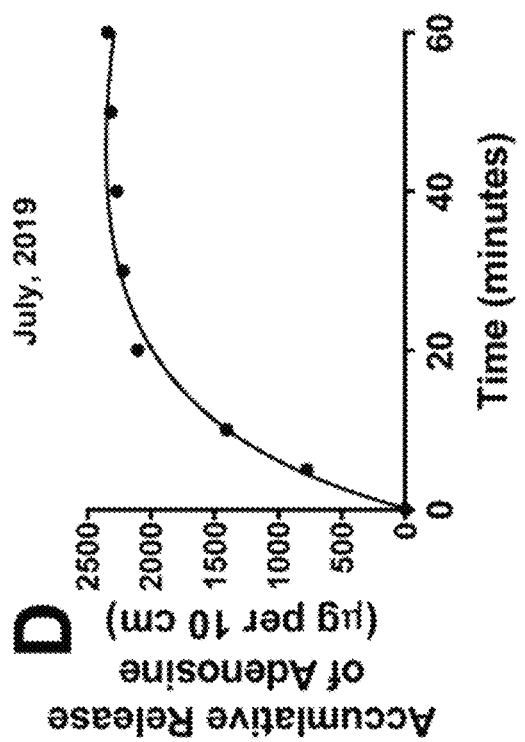
Figure 24C:
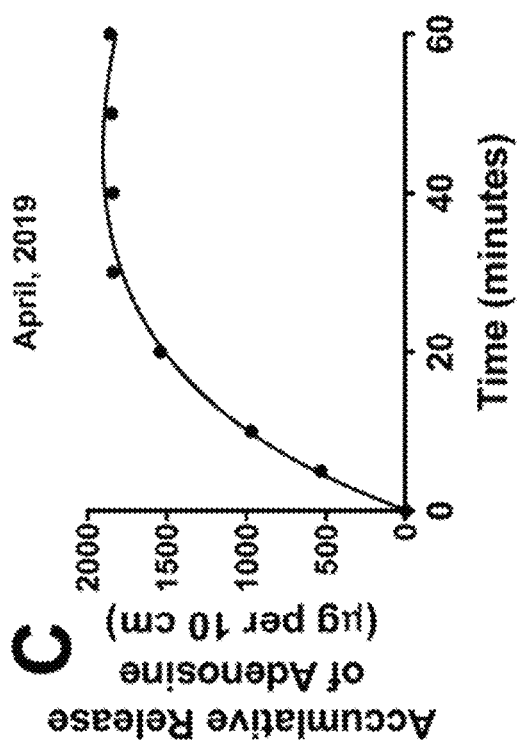
Figure 24F:
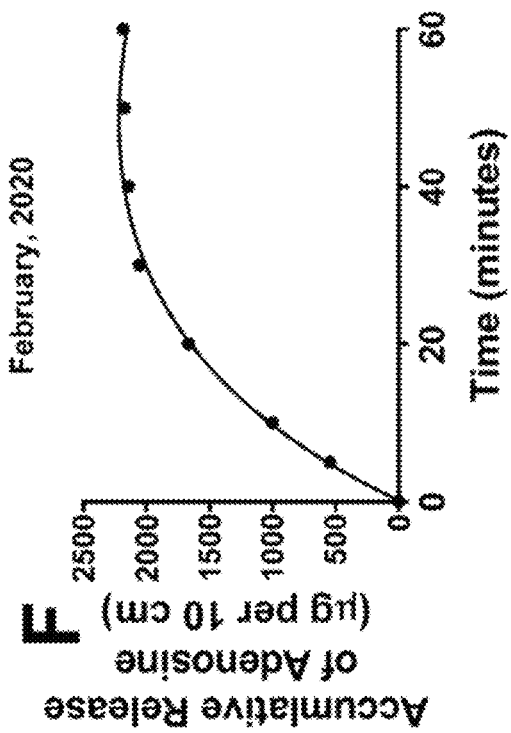
Figure 24E:
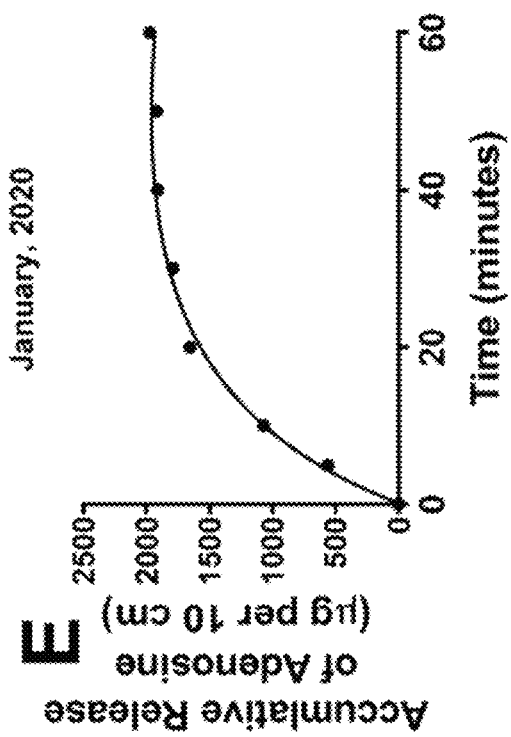
Figure 24H:
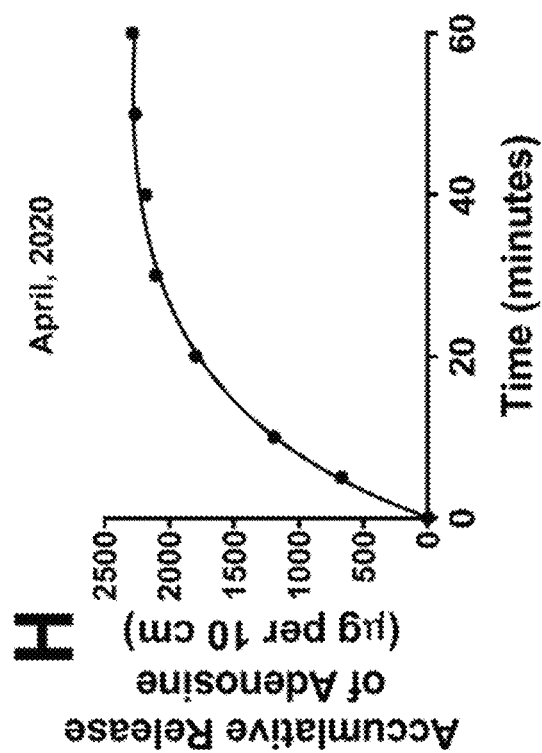
Figure 24G:
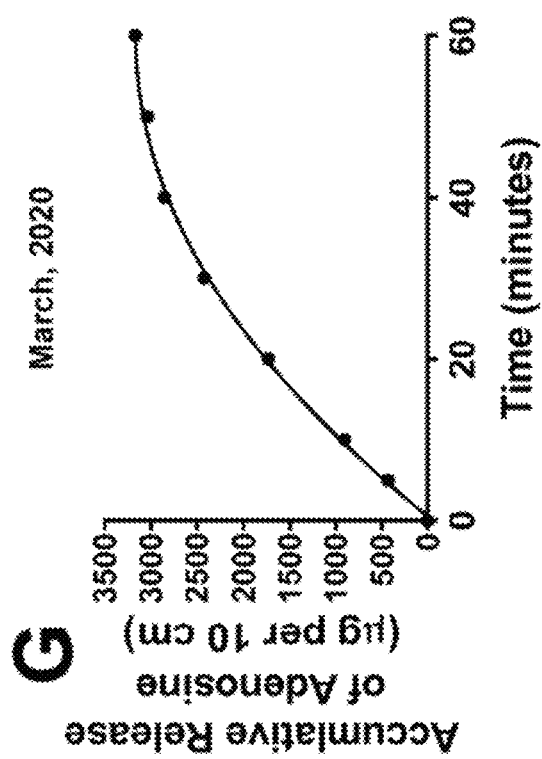

FIGS. 24A-H show historical evolution from November 2018 to April 2020 of different coating formulations and applications and drug size modification to obtain a smooth coating surface with an optimal elution profile for a percutaneous coronary intervention (PCI) procedure. FIG. 24A: rapid release of adenosine with a single layer coating; FIG. 24B: development of a second barrier layer with low polymer mass; FIG. 24C: Utilization of PVAC in barrier coat with overall low polymer mass; FIG. 24D: employed new manual coating technique and increased polymer mass; FIG. 24E: Electronic coating machine used with varying ratios of PVAC with PVA in barrier layer; FIG. 24F: Jet milled adenosine was manufactured to reduce particle size and improve dispersion in hydrogel resulting on smooth coating surface; FIG. 24G: Total polymer weight increased resulting in prolonged elution profile; FIG. 24H: Reduction in coating mass producing an ideal elution profile for PCI procedure.

h. Example 7

Platelet Aggregation Studies. Human venous blood was obtained from 4 healthy donors who had not taken any medications known to influence platelet function for at least 2 weeks prior to the study. Venous blood samples were collected into 3.2% trisodium citrate Vacutainer tubes. After 15 minutes the tubes were centrifuged at 200 g for 10 minutes at room temperature to recover platelet rich plasma (PRP). Platelet-poor plasma (PPP) was then obtained by centrifuging PRP at 1500 g for 10 minutes. 200 uL of PRP were transferred to aggregation curvettes with stir bars. One cm pieces of guidewires with (Adenowire) and without adenosine (Control) were added to the curvette and incubated in a multiple channel optical aggregometer (Chrono-Log, Corp, Hovertown, PA) and stirred for 20 minutes. Two commercially available guidewires, BMW (Abbott Vascular, Santa Clara, CA)) and Runthrough NS (Terumo, Tokyo, Jp), were also evaluated. Following incubation, PRP was transferred to fresh curvettes with stir bars and aggregation was initiated by adding 2 μM ADP or 1 μg/ml collagen and monitored for 6 minutes. Maximal aggregation utilizing PPP as a control reference was assessed with the use of the Platelet Aggregation Monitoring and Analysis software package. Maximal aggregation (amplitude), area under the curve and slope were the readout parameters included in the analysis. Data are expressed as mean±SEM and were analyzed with 1 factor ANOVA followed by Fischer's LSD test.

Figure 25A:
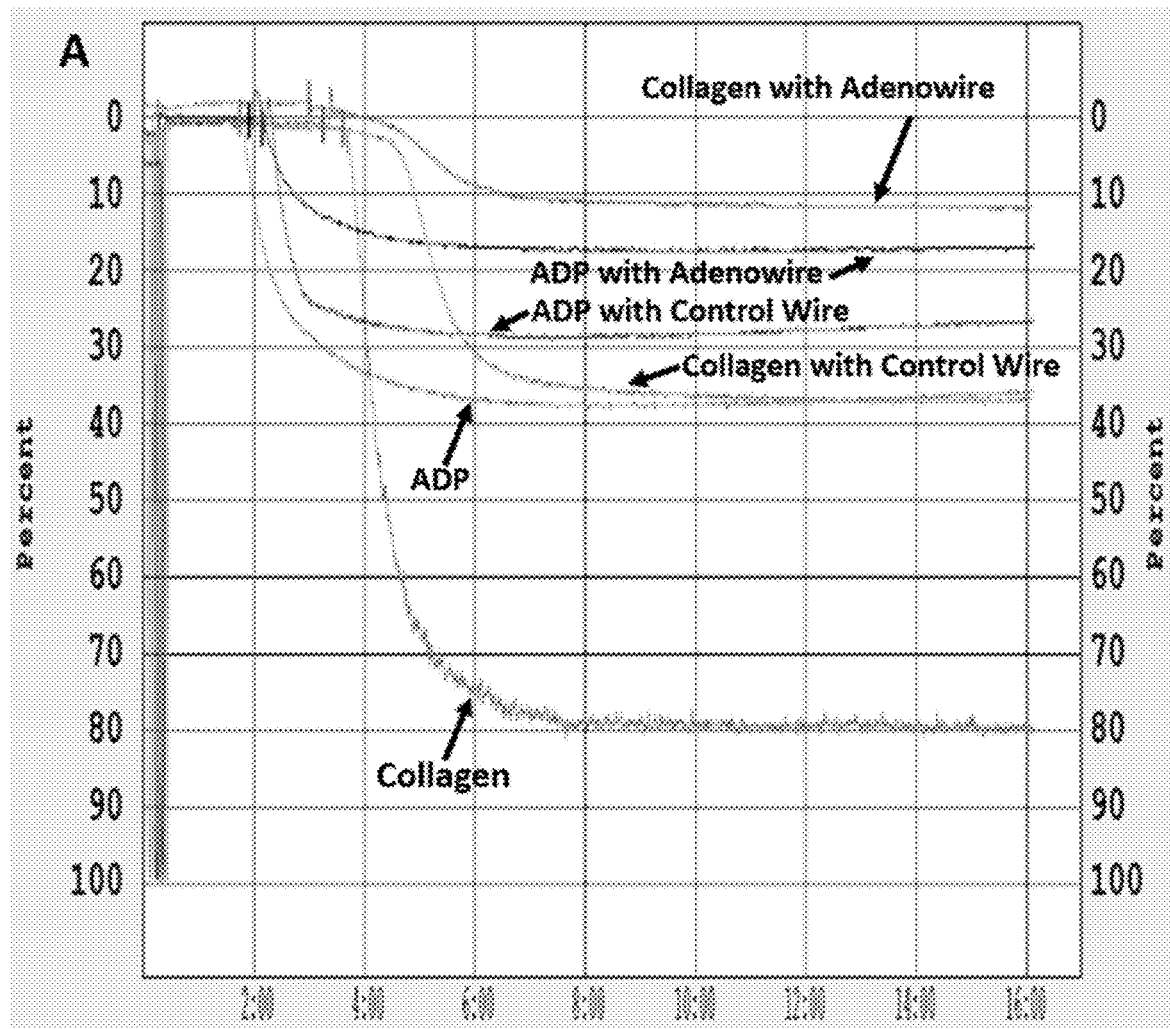

Since 1 cm length of Adenowire contains ~0.27 mg of adenosine, the concentration of adenosine present in the 0.2 ml of PRP would be estimated to be 5 mM assuming total release of adenosine (0.27 mg/0.2 ml=1350 mg/L=5 mM). Thus, there should be a sufficient concentration of adenosine to attenuate platelet activation. FIG. 25 illustrates the effects of Adenowires and Control wires (wires coated with the novel coating formulation but without adenosine) on area under the aggregation curve (AUC), maximum aggregation, rate of aggregation (slope) and lag time between addition of agonist and the onset of aggregation. The coated wires containing adenosine (Adenowires) resulted in a striking inhibition of ADP-induced and collagen-induced platelet aggregation as assessed by the reduction in AUC, maximum aggregation and rate of aggregation. In addition, Adenowires delayed aggregation in response to collagen. Unexpectedly, Control wires exerted anti-platelet effects that were similar to Adenowires but not quite as striking. Moreover, Control wires exerted more efficacious platelet inhibition compared to two commercially-available hydrophilic wires (AUC: Control wires, 116±30 vs. commercial wires, 258±32, P<0.05; Maximum Aggregation: Control wires, 28±6 vs. commercial wires, 62±8, P<0.05).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A guidewire comprising:
   a) a plurality of coils having spaces therebetween ranging from about 0.075 mm to about 0.123 mm;
   b) a primer layer attached to the plurality of coils covalently via silane coupling, the primer layer comprising methoxy-capped polyethylene glycol (PEG); and
   c) a hydrogel coating attached to the primer layer via hydrogen bonds, the hydrogel coating comprising:
      i) water,
      ii) a polymer selected from polyvinyl alcohol (PVA), polyvinyl acetate (PVAc), polyethylene glycol (PEG), poly(methyl acrylate), poly(ethyl acrylate), poly(methyl methacrylate), poly(acrylic acid), or a blend, combination, or copolymer thereof,
      iii) polyvinylpyrrolidone (PVP), and
      iv) a therapeutic agent;
   wherein the hydrogel coating is present on the plurality of coils and in the spacing between the coils.

2. The guidewire of claim 1, further comprising an outer diffusive barrier layer over the hydrogel coating, the outer diffusive barrier layer comprising PVA, PVAc, PVP, PEG, or a blend, combination, or copolymer thereof.

3. The guidewire of claim 2, wherein the outer diffusive barrier layer comprises PVA and PVAc.

4. The guidewire of claim 2, wherein the outer diffusive barrier layer comprises a PVA-PEG copolymer blended with PVAc.

5. The guidewire of claim 1, wherein the therapeutic agent inhibits platelet aggregation.

6. The guidewire of claim 1, wherein the therapeutic agent dilates a plurality of blood vessels.

7. The guidewire of claim 1, wherein the therapeutic agent is a calcium-channel blocker.

8. The guidewire of claim 1, wherein the therapeutic agent is diltiazem.

9. The guidewire of claim 1, wherein the therapeutic agent is adenosine or an adenosine analog.

10. The guidewire of claim 1, wherein the plurality of coils have spaces therebetween ranging from about 0.1 mm to about 0.123 mm.

11. The guidewire of claim 1, wherein the therapeutic agent is dispersed or dissolved in the hydrogel and incorporated in or bound to a solubilizing agent.

12. The guidewire of claim 11, wherein the solubilizing agent is a cylcodextrin.

13. The guidewire of claim 1, wherein the therapeutic agent has an average particle size of less than about 10 microns.

14. The guidewire of claim 13, wherein the therapeutic agent has an average particle size of less than about 5 microns.

15. The guidewire of claim 1, wherein the guidewire comprises stainless steel.

16. The guidewire of claim 1, wherein the guidewire has a surface area of from about 0.021 square inches to about 0.500 square inches.

17. The guidewire of claim 1, wherein the hydrogel coating releases a therapeutic amount of the therapeutic agent over a time period of from about 0.5 minutes to about 120 minutes when in contact with a body fluid.

18. The guidewire of claim 1, wherein the hydrogel coating releases the therapeutic agent at a rate of from about 20 mcg/min to about 1,000 mcg/min when in contact with a body fluid.

19. A method for treating vascular or organ damage in a subject, the method comprising inserting the guidewire of claim 1 into the subject's artery, vein, or cardiac chamber.

* * * * *